United States Patent
Ikeda et al.

(10) Patent No.: US 11,987,904 B2
(45) Date of Patent: May 21, 2024

(54) OLIGONUCLEOTIDES AND METHODS FOR PREPARING

(71) Applicant: Aptamer Group Limited, York (GB)

(72) Inventors: Shuji Ikeda, London (GB); Shozo Fujita, London (GB); Tsuyoshi Fujihara, London (GB)

(73) Assignee: APTAMER GROUP LIMITED, York (GB)

(*) Notice: Subject to any disclaimer, the term of this patent is extended or adjusted under 35 U.S.C. 154(b) by 1581 days.

(21) Appl. No.: 16/081,635

(22) PCT Filed: Mar. 2, 2017

(86) PCT No.: PCT/EP2017/054963
§ 371 (c)(1),
(2) Date: Aug. 31, 2018

(87) PCT Pub. No.: WO2017/149097
PCT Pub. Date: Sep. 8, 2017

(65) Prior Publication Data
US 2023/0132627 A1    May 4, 2023

(30) Foreign Application Priority Data
Mar. 4, 2016 (GB) .................................. 1603789

(51) Int. Cl.
*C40B 40/06* (2006.01)
*C12N 15/10* (2006.01)
(Continued)

(52) U.S. Cl.
CPC .......... *C40B 40/08* (2013.01); *C12N 15/1093* (2013.01); *C12N 15/115* (2013.01);
(Continued)

(58) Field of Classification Search
None
See application file for complete search history.

(56) References Cited

U.S. PATENT DOCUMENTS 7,517,646 B2    4/2009  Fujihara et al.
7,723,495 B2    5/2010  Fujihara et al.
(Continued)

FOREIGN PATENT DOCUMENTS

JP    5365005 B2    12/2013
WO    9306121 A1    4/1993
(Continued)

OTHER PUBLICATIONS

International Search Report and Written Opinion, dated Aug. 18, 2017, corresponding to International Application No. PCT/EP2017/054963; 22 total pages.
(Continued)

*Primary Examiner* — Christian C Boesen
(74) *Attorney, Agent, or Firm* — Carter, DeLuca & Farrell LLP

(57) ABSTRACT

Oligonucleotide constructs are described, each comprising a functional element and a coding element, wherein the functional element comprises a functional sequence, the functional sequence comprising a sequence of nucleotides in which one or more, or each, nucleotide is modified and the coding element comprises a coding sequence, the coding sequence comprising a sequence of nucleotides which do not contain the modifications of the functional sequence, wherein the coding sequence encodes the sequence structure of the functional sequence.

13 Claims, 18 Drawing Sheets

Specification includes a Sequence Listing.

(51) Int. Cl.
*C12N 15/115* (2010.01)
*C40B 40/08* (2006.01)

(52) U.S. Cl.
CPC ...... *C12N 2310/16* (2013.01); *C12N 2310/52* (2013.01); *C12N 2320/11* (2013.01); *C12N 2330/31* (2013.01)

(56) References Cited

U.S. PATENT DOCUMENTS

| | | |
|---|---|---|
| 7,759,473 B2 | 7/2010 | Fujihara et al. |
| 7,910,726 B2 | 3/2011 | Fujihara |
| 7,951,533 B2 | 5/2011 | Fujihara et al. |
| 8,288,516 B2 | 10/2012 | Fujihara et al. |
| 8,299,225 B2 | 10/2012 | Fujihara |
| 8,759,502 B2 | 6/2014 | Fujihara |
| 8,889,843 B2 | 11/2014 | Fujihara |
| 8,940,879 B2 | 1/2015 | Fujihara et al. |
| 2009/0011957 A1 | 1/2009 | Gouliaev et al. |
| 2011/0151510 A1 | 6/2011 | Fujihara et al. |
| 2014/0100120 A1 | 4/2014 | Gorenstein et al. |
| 2015/0167055 A1 | 6/2015 | Fujihara et al. |

FOREIGN PATENT DOCUMENTS

| | | |
|---|---|---|
| WO | 9320242 A1 | 10/1993 |
| WO | 03078625 A2 | 9/2003 |
| WO | 2004083427 A2 | 9/2004 |
| WO | 2004110964 A2 | 12/2004 |
| WO | 2009012410 A1 | 1/2009 |
| WO | 2009077173 A2 | 6/2009 |
| WO | 2010091144 A1 | 8/2010 |
| WO | 2015091207 A1 | 6/2015 |

OTHER PUBLICATIONS

Yang et al., "Construction and selection of bead-bound combinatorial oligonucleoside phosphorothioate and phosphorodithioate aptamer libraries designed for rapid PCR-based sequencing," Nucleic Acids Research, 2002, vol. 30, No. 23 e132, pp. 1-8.

Yang et al., "Immunofluorescence assay and flow-cytometry selection of bead-bound aptamers," Nucleic Acids Research, 2003, vol. 31, No. 10 e54, pp. 1-8.

Fujita et al., "Novel Protein Detection System Using DNA as Constituent Material," Sci. Tech. J., Apr. 2012, vol. 48, No. 2, pp. 237-243.

Carriero et al., "Solid-Phase Synthesis of Branched Oligonucleotides," Current Protocols in Nucleic Acid Chemistry (2002), Unit 4.14; 1-4,;14.32; 32 pages.

| n=2 5' 3' | A | C | G | T |
|---|---|---|---|---|
| A | $F_0$ | $F_1$ | $F_2$ | $F_3$ |
| C | $F_4$ | $F_5$ | $F_6$ | $F_7$ |
| G | $F_8$ | $F_9$ | $F_a$ | $F_b$ |
| T | $F_c$ | $F_d$ | $F_e$ | $F_f$ |

Figure 9B

| n=2 3' \ 5' | A | C | G | T |
|---|---|---|---|---|
| A | $T_{Pro}$ | $C_{Phe}$ | $C_{Ile}$ | $T_{Tyr}$ |
| C | $T_{Ser}$ | $C_{Ala}$ | $C_{Thr}$ | $T_{Gly}$ |
| G | $T_{Val}$ | $C_{His}$ | $C_{Leu}$ | $T_{Gln}$ |
| T | $T_{Cys}$ | $C_{Aps}$ | $C_{Asn}$ | $T_{Lys}$ |

Figure 11A

| n=2 3' \ 5' | A | C | G | T |
|---|---|---|---|---|
| A | $AA_{Pro}$ | $C_{Phe}A$ | $G_{Ile}A$ | $T_{Tyr}A$ |
| C | $A_{Ser}C$ | $C_{Ala}C$ | $GC_{Thr}$ | $TC_{Gly}$ |
| G | $AG_{Val}$ | $CG_{His}$ | $GG_{Leu}$ | $T_{Gln}G$ |
| T | $A_{Cys}T$ | $CT_{Aps}$ | $G_{Asn}T$ | $TT_{Lys}$ |

| n=2 5' 3' | A | C | G | T |
|---|---|---|---|---|
| A | $U_{Ala}$ | $C_{Ala}$ | $U_{Asp}$ | $C_{Asp}$ |
| C | $U_{Glu}$ | $C_{Glu}$ | $U_{Gly}$ | $C_{Gly}$ |
| G | $U_{Ile}$ | $C_{Ile}$ | $U_{Lys}$ | $C_{Lys}$ |
| T | $U_{Phe}$ | $C_{Phe}$ | $U_{Ser}$ | $C_{Ser}$ |

——— Fixed sequence
═══ Fixed complementary sequence
▬▬▬ Functional sequence

SEQUENCE LISTING

<160> NUMBER OF SEQ ID NOS: 2

<210> SEQ ID NO 1
<211> LENGTH: 13
<212> TYPE: RNA
<213> ORGANISM: Artificial Sequence
<220> FEATURE:
<223> OTHER INFORMATION: functional nucleotide sequence
<220> FEATURE:
<221> NAME/KEY: misc_feature
<222> LOCATION: (1)..(1)
<223> OTHER INFORMATION: A nucleotide with an alanine side chain
<220> FEATURE:
<221> NAME/KEY: misc_feature
<222> LOCATION: (2)..(2)
<223> OTHER INFORMATION: A nucleotide with a glutamic acid side chain
<220> FEATURE:
<221> NAME/KEY: misc_feature
<222> LOCATION: (3)..(3)
<223> OTHER INFORMATION: A nucleotide with a phenylalanine side chain
<220> FEATURE:
<221> NAME/KEY: misc_feature
<222> LOCATION: (4)..(4)
<223> OTHER INFORMATION: A nucleotide with a threonine side chain
<220> FEATURE:
<221> NAME/KEY: misc_feature
<222> LOCATION: (5)..(5)
<223> OTHER INFORMATION: A nucleotide with a tryptophan side chain
<220> FEATURE:
<221> NAME/KEY: misc_feature
<222> LOCATION: (6)..(6)
<223> OTHER INFORMATION: A nucleotide with an aspartic acid side chain
<220> FEATURE:
<221> NAME/KEY: misc_feature
<222> LOCATION: (7)..(7)
<223> OTHER INFORMATION: A nucleotide with a serine side chain
<220> FEATURE:
<221> NAME/KEY: misc_feature
<222> LOCATION: (8)..(8)
<223> OTHER INFORMATION: A nucleotide with a valine side chain
<220> FEATURE:
<221> NAME/KEY: misc_feature
<222> LOCATION: (9)..(9)
<223> OTHER INFORMATION: A nucleotide with a lysine side chain
<220> FEATURE:
<221> NAME/KEY: misc_feature
<222> LOCATION: (10)..(10)
<223> OTHER INFORMATION: A nucleotide with an histidine side chain
<220> FEATURE:
<221> NAME/KEY: misc_feature
<222> LOCATION: (11)..(11)
<223> OTHER INFORMATION: A nucleotide with a glutamic acid side chain
<220> FEATURE:
<221> NAME/KEY: misc_feature
<222> LOCATION: (12)..(12)
<223> OTHER INFORMATION: A nucleotide with a glycine side chain
<220> FEATURE:
<221> NAME/KEY: misc_feature
<222> LOCATION: (13)..(13)
<223> OTHER INFORMATION: A nucleotide with a tyrosine side chain

<400> SEQUENCE: 1
agcugccauu gcu                                                          13

<210> SEQ ID NO 2
<211> LENGTH: 13
<212> TYPE: RNA
<213> ORGANISM: Artificial Sequence
<220> FEATURE:
<223> OTHER INFORMATION: functional nucleotide sequence
<220> FEATURE:
<221> NAME/KEY: misc_feature
<222> LOCATION: (1)..(1)
<223> OTHER INFORMATION: a nucleotide with an alanine side chain
<220> FEATURE:
<221> NAME/KEY: misc_feature

```
<222> LOCATION: (2)..(2)
<223> OTHER INFORMATION: a nucleotide with a glutamic acid side chain
<220> FEATURE:
<221> NAME/KEY: misc_feature
<222> LOCATION: (6)..(6)
<223> OTHER INFORMATION: a nucleotide with an aspartic acid side chain
<220> FEATURE:
<221> NAME/KEY: misc_feature
<222> LOCATION: (7)..(7)
<223> OTHER INFORMATION: a nucleotide with a serine side chain
<220> FEATURE:
<221> NAME/KEY: misc_feature
<222> LOCATION: (8)..(8)
<223> OTHER INFORMATION: a nucleotide with a valine side chain
<220> FEATURE:
<221> NAME/KEY: misc_feature
<222> LOCATION: (9)..(9)
<223> OTHER INFORMATION: a nucleotide with a lysine side chain
<220> FEATURE:
<221> NAME/KEY: misc_feature
<222> LOCATION: (10)..(10)
<223> OTHER INFORMATION: a nucleotide with an histidine side chain
<220> FEATURE:
<221> NAME/KEY: misc_feature
<222> LOCATION: (11)..(11)
<223> OTHER INFORMATION: a nucleotide with a glutamic acid side chain
<220> FEATURE:
<221> NAME/KEY: misc_feature
<222> LOCATION: (12)..(12)
<223> OTHER INFORMATION: a nucleotide with a glycine side chain
<220> FEATURE:
<221> NAME/KEY: misc_feature
<222> LOCATION: (13)..(13)
<223> OTHER INFORMATION: a nucleotide with a tyrosine side chain

<400> SEQUENCE: 2
agcugccauu gcu                                                          13
```

OLIGONUCLEOTIDES AND METHODS FOR PREPARING

CROSS REFERENCE TO RELATED APPLICATION

The present application is a 371 application of International Patent Application No. PCT/EP2017/054963 filed on Mar. 2, 2017 which claims priority to United Kingdom Patent Application No. 1603789.7 filed on Mar. 4, 2016, the contents of which are hereby incorporated by reference herein for all purposes.

FIELD OF THE INVENTION

The present invention relates to oligonucleotide constructs and their use in the selection and identification of oligonucleotides having a property of interest.

BACKGROUND TO THE INVENTION

Aptamers, also called nucleic acid ligands, are a class of nucleic acid molecule identified by the SELEX process (Systematic Evolution of Ligands by EXponential enrichment) and characterised by the ability to bind a target molecule with high specificity and high affinity. The binding interaction relies on the three dimensional structure of the nucleic acid rather than complementary binding of bases (hybridisation). Aptamers and SELEX are described in Tuerk and Gold (Systematic evolution of ligands by exponential enrichment: RNA ligands to bacteriophage T4 DNA polymerase. Science. 1990 Aug. 3; 249(4968):505-10) and in WO91/19813. SELEX is an iterative process in which a library of candidate nucleic acids is screened for ability to bind a target molecule, binding nucleic acids are partitioned from non-binding nucleic acids, amplified (e.g. by the polymerase chain reaction (PCR)) and then re-screened until a small number of nucleic acids having high affinity for the target molecule can be identified.

Although SELEX can be performed with some modified nucleotides, the extent of useful modifications can be limited by the ability of polymerase enzymes to accept the modified nucleotide as a substrate. In this context, an alternative technique for identifying modified oligonucleotides, so-called X-aptamers, is described in US 2014/0100120 A1. In this technique a bead based combinatorial library of X-aptamers is prepared in which each bead of the library comprises more than one copy of a unique oligonucleotide (base sequence and modifications). The library may be screened against a target molecule and individual beads (and therefore X-aptamers) selected. A continuing disadvantage of this approach is that the polymerase based amplification used to determine the sequence of the X-aptamer still requires the use of an unmodified copy (proxy) of the X-aptamer to which coding information must then be applied in order to indicate which of the unmodified nucleotides in the proxy are modified in the selected X-aptamer. In turn, this limits the range of chemical modifications that may be used to those that can be read by the polymerase used in the amplification step.

Bead-based formation of random library, i.e. split and mix methodology, and determination of structure after identifying a functional molecule from the library are reported by Lik Hang Yuen et al. J. Amer. Chem. Soc., 136, pp14576-14582 (2014) and Michael H. J. Ohlmeyer et al., Proc. Natl. Acad. Sci. USA, 90, pp10922-10926 (1993). The former discloses tetramer oligonucleotide library composed of 9 modified nucleotides. It uses MALDI-TOF mass spectroscopy of the molecule to identify its structure. The latter discloses hexamer peptide library with tag molecule which is suited for gas chromatography after UV irradiation. Neither method is reasonably applicable to longer oligonucleotides.

U.S. Pat. No. 7,517,646B2 describes a non-SELEX derived functional oligonucleotide molecule that can be selected to have high affinity and specificity to a target molecule. The functional oligonucleotide comprises a contiguous string of nucleotide n-mers, where n is always 2 or more. For example, where n=2 the oligonucleotide comprises a contiguous string of di-nucleotides. One nucleotide in each n-mer is a modified nucleotide, the remaining nucleotide(s) being non-modified. The unique base sequence of each n-mer thereby encodes the type of modification contained on the modified nucleotide. The base sequence (or n-mer sequence) of the oligonucleotide therefore encodes the pattern of modifications present and by reading the base sequence in a 5' to 3' direction in units of n the modification pattern can be determined, The modifications contemplated in U.S. Pat. No. 7,517,646B2 include the 5-position modification of pyrimidine or 7- or 8-position modification of purine by attachment of an amino acid moiety to the pyrimidine or purine base, each unique n-mer having a different amino acid side chain. Other modifications are disclosed in U.S. Pat. No. 8,940,879B2 in which the amine group of the nucleoside base at the 6-position of adenine, 2-position of guanine or 4-position of cytosine is used for attachment. Examples of modified nucleotides are also disclosed in U.S. Pat. Nos. 7,910,726B2 and 8,759,502B2.

As such, the functional oligonucleotides described in U.S. Pat. Nos. 7,517,646B2, 8,940,879B2, 7,910,726B2 and 8,759,502B2 provide an oligonucleotide scaffold modified to contain a number of amino acid moieties available to interact with a given target, e.g. a protein. The oligonucleotide therefore presents a series of amino acids, in particular amino acid side chains, which are available to bind candidate targets. The interaction of oligonucleotide and target mimics that of proteinaceous or peptide binding agents, e.g. antibodies or antibody fragments, in which amino acids and their side chains form the binding site/interface. By preparing a library of oligonucleotides differing in the order and composition of the n-mer units a large number ($4^n$) of oligonucleotide molecules that differ in the composition and sequence of amino acid side chains can be prepared and screened for target binding.

As with the situation described in US 2014/0100120 A1, in order to determine the sequence of n-mers in a selected functional oligonucleotide, and thereby determine the amino acid side chain sequence of the oligonucleotide, the modifications are required to be removed from each base in order to allow the use of polymerase based amplification techniques (e.g. PCR). For example, the two step deprotection method described in US 2015/0167055A1 involves removal of all modified side chains, e.g. by treatment with aqueous ammonia, sodium hydroxide, or hydrofluoric acid and fluoride. As a result, the functional oligonucleotide is destroyed during decoding of its modification pattern and requires synthesis de novo thereafter. This characteristic of the functional oligonucleotides described in U.S. Pat. No. 7,517,646B2 is also why they are not SELEX identifiable aptamers, the SELEX process relying on faithful amplification of the nucleic acid sequences between rounds of target binding.

In order to provide sufficient sequence space to accommodate a useful number of different base modifications U.S.

Pat. No. 7,517,646B2 discloses the minimum value of n for each n-mer to be 2. This has the effect that an amino acid moiety is only presented by a minimum of every other nucleotide, requiring long oligonucleotide chains to present a given number of amino acid moieties, increasing the space between amino acid side chains and reducing the density of the amino acid moieties; these factors being relevant to the presentation and accessibility of the amino acid side chain moieties to candidate target molecules. Where n=2, the maximum number of di-nucleotides is only 16 meaning that in order to generate libraries of significant structural diversity new coding tables (e.g. see FIGS. 11B and 12B) and new di-nucleotide synthesis is often required, which is a time consuming process.

SUMMARY OF THE INVENTION

The inventors have addressed these problems by providing an oligonucleotide construct comprising two oligonucleotide sequence elements: a functional element containing the modified nucleotides and a coding element capable of being amplified by enzymatic amplification techniques. The two sequence elements are connected, either by a support matrix or directly to form a single molecule. The coding element thereby remains associated with the functional element, which may be used to select oligonucleotide sequences having a desired property.

Amplification and sequencing of the coding element enables determination of the sequence structure, including modifications, of the functional element which can be synthesised according to the determined sequence structure. The oligonucleotide construct may be used to form a random library of modified oligonucleotides, allowing selection of a functional element having affinity for a target molecule or desired biological functions, and allowing identification of the sequence structure of the functional element.

In one aspect of the present invention an oligonucleotide construct is provided, the oligonucleotide construct comprising a functional element and a coding element, wherein the functional element comprises a functional sequence comprising a sequence of nucleotides in which one or more, or each, nucleotide is modified and the coding element comprises a coding sequence comprising a sequence of nucleotides which do not contain the modifications of the functional sequence, wherein the coding sequence encodes the sequence structure of the functional sequence.

Modified nucleotides may, in principle, be of any kind. The modification may be in any part of the nucleotide, e.g. phosphate, sugar or base. In preferred embodiments, modified nucleotides incorporate modifications in the base.

In some embodiments the modified nucleotide(s) of the functional sequence are independently selected to comprise the structure B-L-Func wherein B is independently selected from a pyrimidine or purine base; L is independently selected from a bond or a linker; and Func is a functional substituent.

In some embodiments the functional element and coding element are part of a single linear or branched oligonucleotide. In other embodiments each of the functional element and coding element are attached to a support matrix.

In some embodiments the coding sequence is an oligonucleotide polymer of n-mers, preferably a plurality of different n-mers, where n is an integer of 1 or greater (preferably 2 or greater) and each n-mer corresponds to a single nucleotide in the functional sequence. As such, the coding sequence preferably has n times the number of nucleotides as the functional sequence.

In some embodiments the functional element comprises the functional sequence flanked by two or more oligonucleotide sequences having partial or complete complementarity to each other.

In some embodiments the coding element comprises the coding sequence flanked by two oligonucleotide sequences.

In some embodiments the functional element and coding element are single stranded.

In another aspect of the present invention a method is provided for producing an oligonucleotide molecule the method comprising synthesising an oligonucleotide molecule based on the sequence structure of a functional sequence of an oligonucleotide construct identified by, or identifiable by, a method comprising contacting a mixture of different oligonucleotide constructs according to the present invention with a target molecule under conditions that permit the oligonucleotide construct and target molecule to bind and form an oligonucleotide construct:target molecule complex, partitioning the complexes from unbound oligonucleotides and/or unbound target molecule, identifying an oligonucleotide construct capable of binding to the target molecule, preferably with high affinity, and determining the sequence structure of the functional sequence.

In another aspect of the present invention a method of preparing an oligonucleotide construct is provided, the method comprising synthesising an oligonucleotide construct as described herein.

In another aspect of the present invention a library of oligonucleotide constructs as described herein is provided, wherein the library comprises a plurality of oligonucleotide constructs having different sequence structure of the functional sequence. In some embodiments the oligonucleotide constructs differ in the base sequence of the functional sequence.

In another aspect of the present invention a method of preparing a library of oligonucleotide constructs is provided, the method comprising synthesising a plurality of oligonucleotide constructs, each as described herein, wherein the oligonucleotide constructs have different sequence structure of the functional sequence.

In another aspect of the present invention a method of preparing an oligonucleotide construct is provided, the oligonucleotide construct comprising a functional element and a coding element, the method comprising:
  (i) extension of a functional element by addition of a single modified nucleotide to form a functional sequence,
  (ii) extension of a coding element by addition of a nucleotide n-mer to form a coding sequence, the n-mer selected to encode the structure of said modified nucleotide of step (i), wherein n is an integer of 1 or greater (preferably 2 or greater) and the n-mer does not contain the modification of said modified nucleotide of step (i), wherein either step (i) or (ii) may be performed first and steps (i) and (ii) are performed sequentially.

In some embodiments steps (i) and (ii) may be repeated as necessary to produce a coding sequence having a length n times the length of the functional sequence.

In some embodiments, extension of the coding element may comprise addition of n nucleotide monomers.

In some embodiments the number of extension steps performed (for each of (i) and (ii)) may be one of 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments the oligonucleotide construct may be a branched oligonucleotide, wherein the extension in (i)

comprises addition of a single modified nucleotide to a branch moiety to form a first branch, and the extension in (ii) comprises addition of a nucleotide n-mer to the branch moiety to form a second branch.

In some embodiments each oligonucleotide construct is attached to a solid support and preparation of the oligonucleotide constructs is conducted in accordance with a coding table that describes the relationship between each nucleotide added to the functional sequence and the n-mer added to the coding sequence at a corresponding position, wherein each performance of steps (i) and (ii) forms a round of extension, and wherein between rounds of extension the solid supports are mixed and then divided into $2^x$ parts and at least one or each of the $2^x$ parts is subjected to a further round of extension, where x is the number of n-mers in the coding table.

In another aspect of the present invention a method of preparing a library of oligonucleotide constructs is provided, each oligonucleotide construct attached to a solid support and each oligonucleotide construct comprising a functional element and a coding element, the method comprising:
  providing a plurality of solid supports each attached to a branch moiety, optionally via a spacer or linker moiety, from which a branched oligonucleotide may be synthesised by extension of each branch,
  (i) extension of one branch to form a functional element by addition of a single modified nucleotide to form a functional sequence,
  (ii) extension of another branch to form a coding element by addition of a nucleotide n-mer to form a coding sequence, the n-mer selected to encode the structure of said modified nucleotide of step (i), wherein n is an integer of 1 or greater, preferably 2 or greater, and the n-mer does not contain the modification of said modified nucleotide of step (i),
  wherein either step (i) or (ii) may be performed first and steps (i) and (ii) are performed sequentially.

In some embodiments preparation of the oligonucleotide constructs is conducted in accordance with a coding table that describes the relationship between each nucleotide added to the functional sequence and the n-mer added to the coding sequence at a corresponding position, wherein each performance of steps (i) and (ii) forms a round of extension, and wherein between rounds of extension the solid supports are mixed and then divided into $2^x$ parts and at least one or each of the $2^x$ parts is subjected to a further round of extension, where x is the number of n-mers in the coding table.

In some embodiments steps (i) and (ii) may be repeated as necessary to produce a coding sequence having a length n times the length of the functional sequence.

In some embodiments, extension of the coding element may comprise addition of n nucleotide monomers.

In some embodiments the number of extension steps performed (for each of (i) and (ii)) may be one of 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In another aspect of the present invention an oligonucleotide is provided, the oligonucleotide comprising a functional sequence comprising a sequence of nucleotides in which two or more, or each, nucleotide is modified by incorporation of a functional substituent, and wherein at least two adjacent nucleotides are so modified, wherein each functional substituent is independently selected from a side chain of a natural or non-natural amino acid, optionally not the side chain of glycine (H).

In preferred embodiments at least three or at least four adjacent nucleotides are so modified.

In some embodiments the modified nucleotide(s) are independently selected to comprise the structure B-L-Func wherein B is independently selected from a pyrimidine or purine base; L is independently selected from a bond or a linker; and Func is a functional substituent selected from a side chain of one of Alanine (Ala), Arginine (Arg), Asparagine (Asn), Aspartic Acid (Asp), Cysteine (Cys), Glutamic Acid (Glu), Glutamine (Gln), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), Valine (Val), Selenocysteine (Sec) and Pyrrolysine (Pyl).

In some embodiments the modified nucleotide(s) are independently selected to comprise the structure B-L-Func wherein B is independently selected from a pyrimidine or purine base; L is independently selected from a bond or a linker; and Func is a functional substituent selected from a side chain of one of histidine, serine, leucine, glutamic acid, lysine, phenylalanine, tyrosine and tryptophan.

In some embodiments the modified nucleotide(s) are independently selected to comprise the structure B-L-Func wherein B is independently selected from a pyrimidine or purine base; L is independently selected from a bond or a linker; and Func is a functional substituent selected from a side chain of one of Cit (citrulline), L-DOPA (L-3,4-dihydroxy-phenylalanine), homoarginine, homocysteine, homoleucine, homophenylalanine, homoserine, Nle (norleucine), Nva (norvaline), Orn (ornithine), and phenylglycine In some embodiments the functional sequence is flanked by two or more oligonucleotide sequences having partial or complete complementarity to each other. In some embodiments the oligonucleotide is single stranded.

In another aspect of the present invention a method of preparing an oligonucleotide is provided, the method comprising synthesising an oligonucleotide according to the present invention.

In another aspect of the present invention a method of preparing an oligonucleotide according to the present invention is provided, the method comprising synthesising an oligonucleotide molecule based on the sequence structure of a functional sequence of an oligonucleotide construct identified by, or identifiable by, a method comprising contacting a mixture of different oligonucleotide constructs according to the present invention with a target molecule under conditions that permit the oligonucleotide construct and target molecule to bind and form an oligonucleotide construct:target molecule complex, partitioning the complexes from unbound oligonucleotides and/or unbound target molecule, identifying an oligonucleotide construct capable of binding to the target molecule, preferably with high affinity, and determining the sequence structure of the functional sequence.

In another aspect of the present invention a method of detecting a target molecule is provided, the method comprising contacting an oligonucleotide according to any aspect of the present invention, wherein the oligonucleotide is capable of binding the target molecule, with a sample containing, or suspected of containing, said target molecule, and detecting the formation of an oligonucleotide:target molecule complex.

In another aspect of the present invention a composition comprising an oligonucleotide according to any aspect of the present invention is provided. The oligonucleotide may be provided in isolated and/or purified and/or sterile form.

In another aspect of the present invention a pharmaceutical composition is provided, the pharmaceutical composition comprising an oligonucleotide according to any aspect of the present invention and a pharmaceutically acceptable diluent, carrier or excipient. In another aspect of the present invention a diagnostic composition comprising an oligonucleotide according to any aspect of the present invention is provided.

In another aspect of the present invention a method, optionally an in vitro method, is provided, the method comprising contacting an oligonucleotide according to any aspect of the present invention with a target molecule and forming a complex of said oligonucleotide and target molecule.

In another aspect of the present invention a non-covalent complex, preferably in vitro, is provided, the complex comprising an oligonucleotide according to any aspect of the present invention and a target molecule.

In another aspect of the present invention an oligonucleotide according to any aspect of the present invention is provided for use in a method for treatment of the human or animal body by surgery or therapy or in a diagnostic method practised on the human or animal body.

In another aspect of the present invention an oligonucleotide according to any aspect of the present invention is provided for use in a method of treatment or diagnosis.

In another aspect of the present invention the use of an oligonucleotide according to any aspect of the present invention in the manufacture of a pharmaceutical composition or medicament for use in a method of treatment is provided.

In another aspect of the present invention a method of treating a disease is provided, the method comprising administering an oligonucleotide according to any aspect of the present invention to a subject in need of treatment.

Description

The inventors have designed an oligonucleotide construct that contains a functional element that comprises at least a functional sequence which incorporates structural modification(s), and a coding element comprising at least a coding sequence which is preferably non-modified. The functional and coding sequences may each be contiguous nucleotide sequences. In some embodiments they may contain a fixed sequence, spacer or linker within one or each of the respective coding and functional sequences. Where the spacer or linker is not a nucleotide or oligonucleotide the functional or coding sequence may be considered non-contiguous. The coding sequence is a distinct sequence element from the functional sequence and preferably the coding and functional sequences do not overlap. The coding sequence is either non-modified or contains modifications that permit amplification, e.g. enzyme-based (e.g. polymerase) amplification. The sequence structure, including modification sequence, of the functional sequence may therefore be determined by sequencing the coding sequence without destruction or alteration (e.g. removal or alteration of the modifications) of the functional sequence, or the need to re-synthesise the functional sequence after sequence determination.

The functional sequence may represent a random sequence region, varying between oligonucleotide constructs. Each functional sequence is preferably synthesised such that the nature of each base (e.g. base type and modification type) is encoded by a nucleotide n-mer in the coding sequence, and according to a predetermined code which is stored in a coding table.

A library of oligonucleotide constructs may be provided containing a plurality of unique oligonucleotide constructs, which differ in the sequence structure, including nucleotide modifications, and/or in the associated coding table, of their functional sequences (and in the corresponding base sequence of the coding sequence). The library may contain one of $10^2$, $10^3$, $10^4$, $10^5$, $10^6$, $10^7$, $10^8$, $10^9$, $10^{10}$, or more, different oligonucleotide constructs. Oligonucleotide construct libraries may be screened to identify oligonucleotide constructs, in particular sequences of functional sequences, that have a particular chemical or physical property or function. In some embodiments, oligonucleotide constructs may be screened to identify oligonucleotide constructs, in particular functional sequences, that bind to a target molecule with high affinity and/or specificity.

An oligonucleotide construct may be formed as a single molecule having at least two components: a functional element and a coding element.

In some embodiments the oligonucleotide construct may comprise a single linear or branched oligonucleotide in which the functional element and the coding element are present as distinct, preferably non-overlapping, sequence domains which may optionally be separated by additional nucleotide sequence elements. In some embodiments, non-nucleic acid linkers may be present between the functional and coding elements.

In some embodiments the oligonucleotide construct may comprise at least two oligonucleotide molecules, one forming the functional element and one forming the coding element, each attached to a support matrix, e.g. a bead.

Following identification of an oligonucleotide construct having a functional sequence of interest, the sequence structure of the functional sequence may be determined by sequencing the coding sequence and referring to the coding table to decode the sequence structure of the functional sequence.

In some embodiments, following identification of an oligonucleotide construct having a functional sequence of interest, the sequence of the coding sequence may be determined and, referring to a coding table, decoded to reveal the sequence structure of the functional sequence.

Oligonucleotide molecules comprising at least the sequence of the functional sequence, without the coding sequence or coding element, may then be synthesised de novo.

Oligonucleotide constructs and oligonucleotide molecules according to the present invention may be provided in isolated or purified form. They are preferably non-naturally occurring molecules and may include non-naturally occurring modifications. Functional sequences preferably comprise or consist of non-naturally occurring base sequences or sequence structures (i.e. including modifications).

Oligonucleotides may be DNA, RNA, single stranded or double stranded. Oligonucleotides are preferably single stranded. Oligonucleotides are preferably DNA.

Oligonucleotide constructs, oligonucleotide molecules and functional sequences according to the present invention may be useful in virtually any situation in which target binding is required, including use in therapeutic, diagnostic and research (e.g. research tool) applications, in vitro or in vivo.

Oligonucleotide Construct

Oligonucleotide constructs according to the present invention comprise a functional element comprising at least a functional oligonucleotide sequence (herein referred to as a 'functional sequence') and a coding element comprising at least a coding oligonucleotide sequence (herein referred to as a 'coding sequence').

The functional element comprises a functional sequence intended to contain modifications to the nucleotide, nucleoside or base structure. The functional sequence forms the core of a candidate oligonucleotide which may be screened for physical, chemical or functional properties, such as target binding.

The functional element is intended to provide a functional sequence composed of modified nucleotides, and optionally some non-modified nucleotides. Certain functional sequences (and/or functional elements) may fold and form a three-dimensional structure that allows complementary interaction with, and preferably binding to, a target molecule. These sequences are selectable by appropriate screening.

The coding element comprises a coding sequence intended to encode the sequence structure (nucleotide/base sequence and the specific modifications) of the functional sequence, and is intended to allow facile amplification and sequencing of the coding sequence to allow simple and fast translation of the encoded sequence of the functional sequence. The nucleotide, nucleoside and base modifications present in the functional sequence are preferably absent from the corresponding part of the coding sequence, and are preferably completely absent from the coding sequence.

The functional element and coding element may be covalently linked to form a single contiguous oligonucleotide molecule, e.g. a linear or branched oligonucleotide molecule. Contiguous nucleotide sequences are typically covalently linked by phosphodiester bonds, or similar bonds such as phosphorothioate. In some embodiments, non-nucleic acid linkers may be present between nucleotide sequence elements, e.g. between the functional and coding sequences. Linkers or spacers may provide for either covalent or non-covalent attachment of nucleotide sequence elements. Examples of linkers or spacers include polyethylene glycol molecules, or the use of tag and capture element pairs such as biotin and avidin.

Single molecule oligonucleotide constructs may be linear oligonucleotide molecules. These may be chemically synthesised as a linear oligonucleotide, e.g. by the phosphoramidite method. Phosphoramidite chemistry is an attractive method of chemical oligonucleotide synthesis employing a condensation reaction of nucleoside phosphoroamidite to the nucleoside using tetrazole as an enhancer. The cycle associated with phosphoramidite chemistry-based oligonucleotide chemistry is known in the art. In brief, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle is then repeated to assemble the chain [e.g. see Sinha, N. D.; Biernat, J.; McManus, J.; Köster, H. Nucleic Acids Res. 1984, 12, 4539; and Beaucage, S. L.; Iyer, R. P. (1992). *Tetrahedron* 48 (12): 2223].

In some embodiments single molecule oligonucleotide constructs may take the form of branched oligonucleotides (preferably having two branches), in which the functional element forms one branch and the coding element forms another branch. Branched oligonucleotides may also be chemically synthesised, e.g. using a ribonucleoside bisphosphoramidite as the branch-introduction synthon allowing creation of Y- and V-shaped molecules; see Sandra Carriero and Masad J. Damha., *Current Protocols in Nucleic Acid Chemistry* (2002) 4.14.1-4.14.32; or Masad J. Damha, Steve Zabarylo., *Tetrahedron Letters* Volume 30, Issue 46, 1989, Pages 6295-6298. Extension of two oligonucleotides concurrently may also be achieved from a branching moiety indicated by formula (A) below comprising a glycerol substituted with DMTr group at one OH, 2-cyanoethyl-N, N-diisopropyl phosphoramidite group at another OH and levulinyl group at the residual OH group.

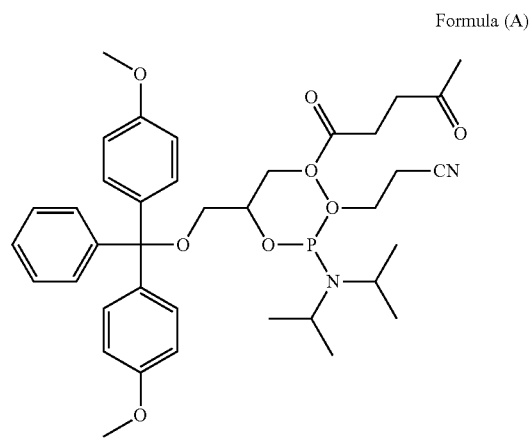

Formula (A)

A longer spacer moiety between the DMTr, phosphoramidite and levulinyl groups may be incorporated to avoid steric hindrance.

Each branch may be synthesised in any chosen direction, e.g. 3' to 5' (5' distal to branch moiety) or 5' to 3' (3' distal to branch moiety). In preferred embodiments the functional element and coding element are each synthesised in 3' to 5' orientation with the 5' end being distal to the branch moiety. A linker oligonucleotide, e.g. used to attach the oligonucleotide construct to a support matrix, may form a third branch and may be synthesised in either orientation. In one embodiment the linker oligonucleotide is formed so that the 5' end is proximal the branch moiety.

Preferably, the functional element and coding element do not overlap and/or the functional sequence and coding sequence do not overlap.

In some embodiments a library of oligonucleotide constructs is provided, the library having a plurality of oligonucleotide constructs differing in the sequence structure of the functional element or functional sequence, optionally differing in the base sequence of the functional element or functional sequence and optionally differing in the corresponding coding element or coding sequence.

In some embodiments an oligonucleotide construct or library may be accompanied by one or more coding tables, allowing the sequence structure of the functional sequence to be determined from the sequence of the coding sequence.

In some embodiments the oligonucleotide construct(s) may incorporate a coding table ID sequence, optionally positioned between fixed sequences that flank the coding sequence and permit enzyme-based amplification. The coding table ID sequence indicates the identity of the correct coding table and allows selection of the correct coding table for the purpose of determining the sequence structure of the functional sequence based on the sequence of the coding sequence. In such embodiments the coding table may have a code or identifier that corresponds to a coding table ID sequence.

Functional Element

A functional element may comprise, or consist of, a functional sequence. Optionally, the functional element may further comprise one, two or more fixed functional sequences, as described below. A functional element is preferably an oligonucleotide molecule, although it may comprise non-nucleotide components, e.g. spacer or linker molecules.

The functional sequence may be a contiguous sequence of nucleotides in which one or more, or all, of the nucleotides are modified, the modification preferably comprising a modified nucleoside (e.g. for RNA: modified adenosine, guanosine, 5-methyluridine, uridine, cytidine, and for DNA: modified deoxyadenosine, deoxyguanosine, thymidine, deoxyuridine, deoxycytidine) or base (e.g. adenine, uracil, guanine, thymine, cytosine). The primary base sequence of the functional sequence will normally vary between oligonucleotide constructs.

The functional sequence may have one, two or more adjacent oligonucleotide sequence(s), e.g. one at the 5' end and one at the 3' end of the functional sequence, thereby flanking the functional sequence. These sequences, each called herein a 'fixed functional sequence', preferably have a predetermined sequence, and are preferably non-random. The functional sequence and fixed functional sequence(s) preferably form a single contiguous oligonucleotide, called herein the 'functional element'. As such, the functional element may comprise, or consist of, a functional sequence and one or more, preferably two or more than two, fixed functional sequences. In some embodiments the functional sequence may therefore be flanked by two fixed functional sequences which each form a contiguous oligonucleotide molecule with the functional sequence. In some embodiments the functional sequence may also have one or more fixed functional sequences inserted at a prefixed position within the functional sequence. This may provide for formation of desired tertiary structures, e.g. see FIG. 15. Fixed functional sequences may be of any convenient length, usually 10 or more, or 15 or more, nucleotides, e.g. between 10 and 40 nucleotides, between 15 and 40 nucleotides or between 15 and 30 nucleotides.

The fixed functional sequences may be designed so as to be partly or completely complementary to each other, thereby promoting double strand formation. This may allow the functional element to form a stem-loop structure in which the functional sequence forms part or all of the loop. The fixed functional sequences may also be designed so as to hybridise to primers for amplification of the functional sequence, e.g. during the Polymerase Chain Reaction (PCR).

Complementary sequences are sequences which may base pair (Watson-Crick base pairing) to form a double stranded (duplex) nucleic acid molecule over the region of complementarity. Partial or complete complementarity of sequences refers to the extent to which two aligned sequences will base pair. Following alignment, complementarity may exist across at least 70% of the aligned sequences. Alternatively, this may be one of 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%. Alignment may be achieved in various ways known to a person of skill in the art, for instance, using publicly available computer software such as ClustalW 1.82. T-coffee or Megalign (DNASTAR) software.

In some embodiments, the functional element may have three or more fixed functional sequences, e.g. one at the 5' end, one inserted at a prefixed position in the functional sequence and one at the 3' end of the functional sequence, the 3' and 5' fixed functional sequences thereby flanking the functional sequence. The functional sequence and fixed functional sequences preferably form a single contiguous functional element. The fixed functional sequences may be designed so as to be partly or completely complementary to each other, thereby promoting double strand formation. This may allow the functional element to form one or a plurality of loop structures in which the functional sequence forms part or all of the loop structures, e.g. see FIG. 15. At least two of the fixed functional sequences (preferably those flanking the functional sequence) may also be designed so as to hybridise to primers for amplification of the functional sequence, e.g. during the Polymerase Chain Reaction (PCR).

Hybridisation of nucleic acids refers to the process in which a single stranded oligonucleotide sequence anneals to another single stranded oligonucleotide sequence (optionally both sequences being elements that are part of a single oligonucleotide) to form a double stranded (duplex) element. Determination of hybridisation provides an alternative means of assessing ability to form double stranded regions over analysis of sequence for complementarity. Complementary nucleic acid sequences will hybridise to one another through Watson-Crick binding interactions. Sequences which are not 100% complementary may also hybridise but the strength of the hybridisation usually decreases with the decrease in complementarity. The strength of hybridisation can therefore be used to distinguish the degree of complementarity of sequences capable of binding to each other.

The "stringency" of a hybridization reaction can be readily determined by a person skilled in the art. The stringency of a given reaction may depend upon factors such as probe length, washing temperature, and salt concentration. Higher temperatures are generally required for proper annealing of long probes, while shorter probes may be annealed at lower temperatures. The higher the degree of desired complementarity between the probe and hybridisable sequence, the higher the relative temperature which can be used. As a result, it follows that higher relative temperatures would tend to make the reaction conditions more stringent, while lower temperatures less so.

For example, hybridizations may be performed, according to the method of Sambrook et al., ("Molecular Cloning, A Laboratory Manual, Cold Spring Harbor Laboratory Press, 1989) using a hybridization solution comprising: 5× SSC, 5× Denhardt's reagent, 0.5-1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2× SSC and 1% SDS; (2) 15 minutes at room temperature in 2× SSC and 0.1% SDS; (3) 30 minutes-1 hour at 37° C. in 1× SSC and 1% SDS; (4) 2 hours at 42-65° C. in 1× SSC and 1% SDS, changing the solution every 30 minutes.

The functional sequence in a functional element may be of any length. However, short nucleotide sequences of 100 nucleotides or less are preferred. The functional sequence may have a length in the range of one of 3-100 nucleotides, 3-90 nucleotides, 3-80 nucleotides, 3-70 nucleotides, 3-60 nucleotides, 3-50 nucleotides, 3-40 nucleotides, 3-30 nucleotides. 3-15 nucleotides. In preferred embodiments, the functional sequence has a length in the range 5-30 nucleotides or 5-15 nucleotides.

The functional sequence may have a minimum length selected from one of 3, 4, 5, 6, 7, 8, 9, 10, 11, 12, 13, 14, or 15 nucleotides and a maximum length selected from one of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. In preferred embodiments the functional sequence may have a length of one of 8, 9, 10, 11, 12, 13, 14, 15, 16, 17, 18, 19, 20, 21, 22, 23, 24, 25 nucleotides. In particularly preferred embodiments the functional sequence has a length of one or 8, 9, 10, 11, 12, 13, 14 or 15 nucleotides. In one preferred embodiment the functional sequence has 13 nucleotides.

The functional sequence comprises a sequence element in which one or more, or each, nucleotide is modified. The functional sequence may contain one of 3, 4, 5, 6, 7, 8, 9, 10, 11, 12, 13, 14, or 15 modified nucleotides. In some preferred embodiments at least two adjacent nucleotides are modified. In some preferred embodiments at least three or at least four adjacent nucleotides are modified. Optionally, 3, 4, 5, 6, 7, 8, 9, 10, 11, 12, 13, 14, or 15 adjacent nucleotides are modified. An adjacent nucleotide refers to the next nucleotide in a single strand of the functional sequence, in either 3' to 5' or 5' to 3 direction.

Modified nucleotides may, in principle, be of any kind. The modification may be in any part of the nucleotide, e.g. phosphate, sugar or base. In preferred embodiments, modified nucleotides incorporate modifications in the base.

Accordingly, in some embodiments a modified nucleotide of the functional element comprises a nucleotide in which the base has the structure B-L-Func wherein, B is independently selected from a pyrimidine or purine base; L is independently selected from a bond or a linker; and Func is a functional substituent.

The base B is attached to a sugar, cyclic or acyclic structure, thereby forming a nucleoside or nucleoside analogue, and the nucleoside or nucleoside analogue is attached to a phosphate group, thereby forming the nucleotide.

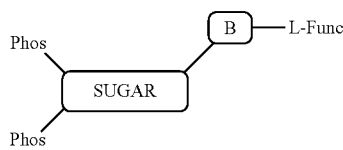

The functional substituent may be of any kind. In some embodiments the functional substituent is independently selected from:
hydrogen;
optionally substituted $C_{1-10}$alkyl;
optionally substituted $C_{2-10}$alkenyl;
optionally substituted $C_{2-10}$alkynyl;
optionally substituted $C_{3-10}$cycloalkyl;
optionally substituted $C_{6-10}$aryl;
optionally substituted $C_{5-10}$heteroaryl;
optionally substituted $C_{3-10}$heterocyclyl;
optionally substituted $C_{1-10}$alkyl-$C_{6-10}$aryl;
optionally substituted $C_{1-10}$alkyl-$C_{5-10}$heteroaryl;
optionally substituted $C_{1-10}$alkyl-$C_{5-10}$cycloalkyl; or
optionally substituted $C_{1-10}$alkyl-$C_{5-10}$heterocyclyl.

In some cases, the functional substituent is selected from: hydrogen; optionally substituted $C_{1-5}$alkyl; optionally substituted phenyl; optionally substituted $C_{5-10}$heteroaryl; optionally substituted $C_{5-10}$heterocyclyl; optionally substituted $C_{1-3}$alkyl-phenyl; optionally substituted $C_{1-3}$alkyl-$C_{5-10}$heteroaryl; optionally substituted $C_{1-3}$alkyl-$C_{5-6}$cycloalkyl; or optionally substituted $C_{1-3}$alkyl-$C_{5-6}$heterocyclyl.

One or more $CH_2$ groups in alkyl substituents may be replaced with —O—.

Alkyl groups having carbon number ranging from 1 to 10 may include, for example, a methyl group, ethyl group, propyl group, isopropyl group, butyl group, isobutyl group, tert-butyl group, pentyl group, neopentyl group, hexyl group, cyclohexyl group, octyl group, nonyl group, decyl group.

In some cases the functional substituent is selected from: thiophene, coenzymes such as but not limited to NAD, NADH, FAD, FADH, pantothenic acid, folic acid, cyanocobalamin, quinone derivatives, cyclothiazide, memantine, buprenorphine, metal complexes, e.g. a ligand coordinated with a metal ion, including, for example, Ru-bipyridil complex, ferrocene complex, nickel imidazole complex, fluorescent dyes, e.g. fluorescein dyes, rhodamine dyes, eosine dyes, NBD dyes, cyanine dyes, oxidation-reduction pigments, e.g. leuco pigments such as leucoaniline, leucoanthocyanine, spin labels, e.g. iron N-( dithiocarboxy) sarcosine, TEMPO (tetramethyl piperidine) derivatives.

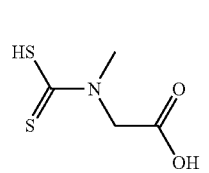 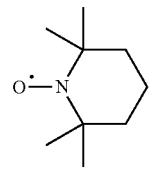

N-(dithiocarboxy) sarcosine     TEMPO (2,2,6,6-tetramethyl-piperidin-1-yl)oxyl

In some embodiments the functional substituent is an amino acid mimetic chemical substituent. For example, it may comprise an amino acid or amino acid side chain. The amino acid or amino acid side chain may be, or from, a natural amino acid or a non-natural amino acid. In some cases, the amino acid is a proteinogenic amino acid. It will be appreciated that when Func is H, the functional substituent mimics glycine. Optionally, in some cases, Func is not H.

Optional substituents may be as described herein. It will be appreciated that, where the functional substituent is an amino acid mimetic, optional substituents are suitably selected from substituents commonly found in natural and non-natural amino acids used in biologically active proteinaceous sequences.

For example, optional substituents may include —OH, —OMe, —SH, —SMe, —NH$_2$. —COOH, —CONH$_2$, —NHCNNH$_2$ and imidazole.

In some embodiments, B-L-Func is selected from:

(1)

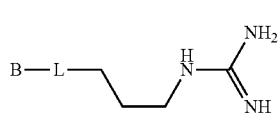
(2)

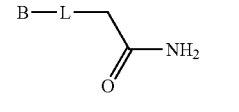
(3)

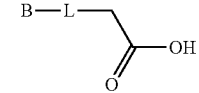
(4)

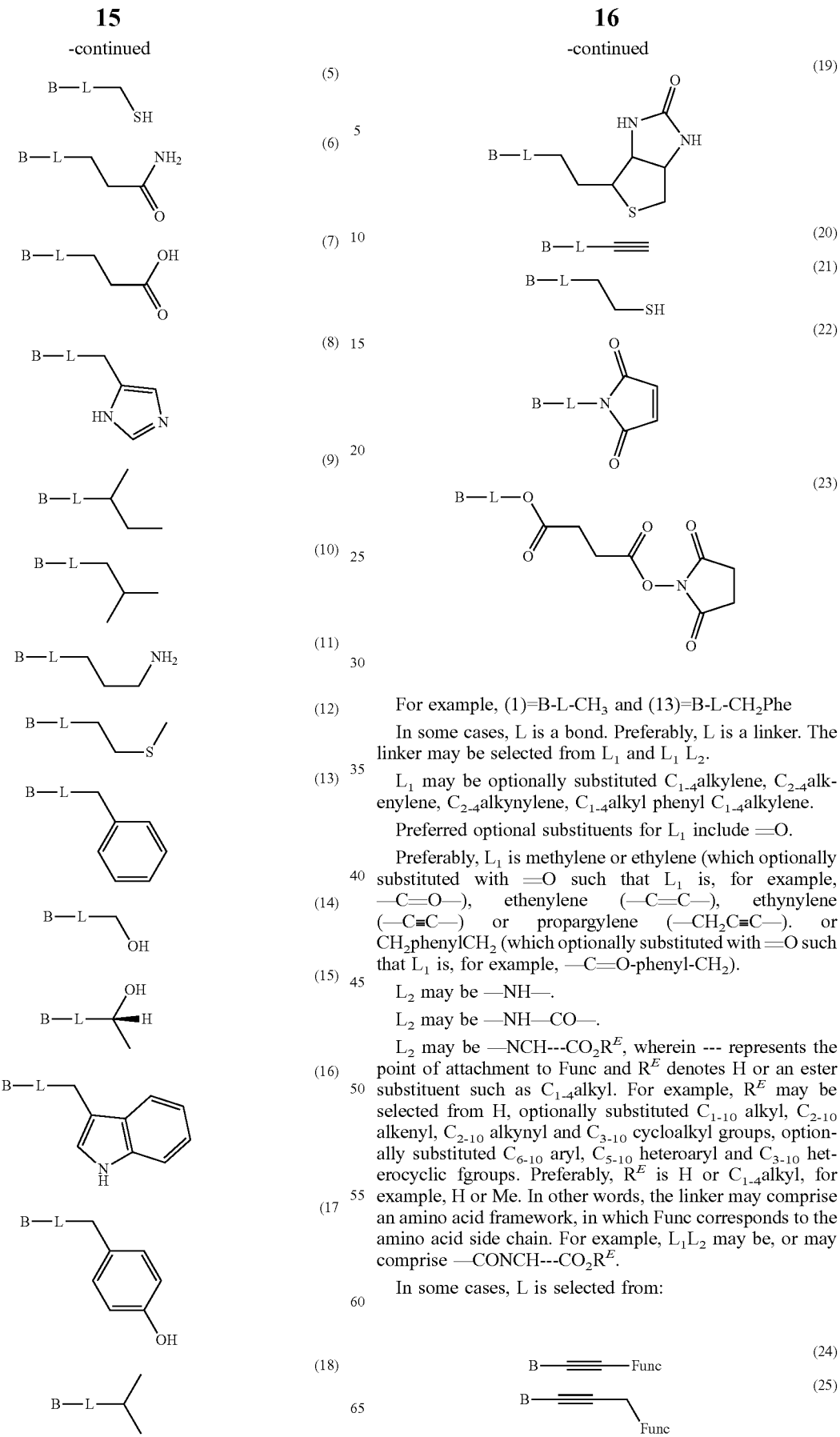

For example, (1)=B-L-CH$_3$ and (13)=B-L-CH$_2$Phe

In some cases, L is a bond. Preferably, L is a linker. The linker may be selected from L$_1$ and L$_1$ L$_2$.

L$_1$ may be optionally substituted C$_{1-4}$alkylene, C$_{2-4}$alkenylene, C$_{2-4}$alkynylene, C$_{1-4}$alkyl phenyl C$_{1-4}$alkylene.

Preferred optional substituents for L$_1$ include =O.

Preferably, L$_1$ is methylene or ethylene (which optionally substituted with =O such that L$_1$ is, for example, —C=O—), ethenylene (—C=C—), ethynylene (—C≡C—) or propargylene (—CH$_2$C≡C—). or CH$_2$phenylCH$_2$ (which optionally substituted with =O such that L$_1$ is, for example, —C=O-phenyl-CH$_2$).

L$_2$ may be —NH—.

L$_2$ may be —NH—CO—.

L$_2$ may be —NCH---CO$_2$R$^E$, wherein --- represents the point of attachment to Func and R$^E$ denotes H or an ester substituent such as C$_{1-4}$alkyl. For example, R$^E$ may be selected from H, optionally substituted C$_{1-10}$ alkyl, C$_{2-10}$ alkenyl, C$_{2-10}$ alkynyl and C$_{3-10}$ cycloalkyl groups, optionally substituted C$_{6-10}$ aryl, C$_{5-10}$ heteroaryl and C$_{3-10}$ heterocyclic fgroups. Preferably, R$^E$ is H or C$_{1-4}$alkyl, for example, H or Me. In other words, the linker may comprise an amino acid framework, in which Func corresponds to the amino acid side chain. For example, L$_1$L$_2$ may be, or may comprise —CONCH---CO$_2$R$^E$.

In some cases, L is selected from:

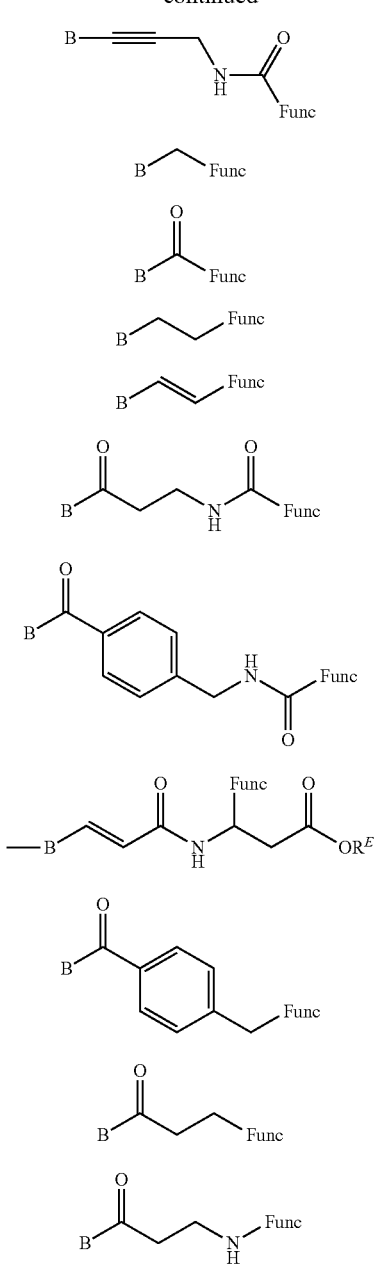

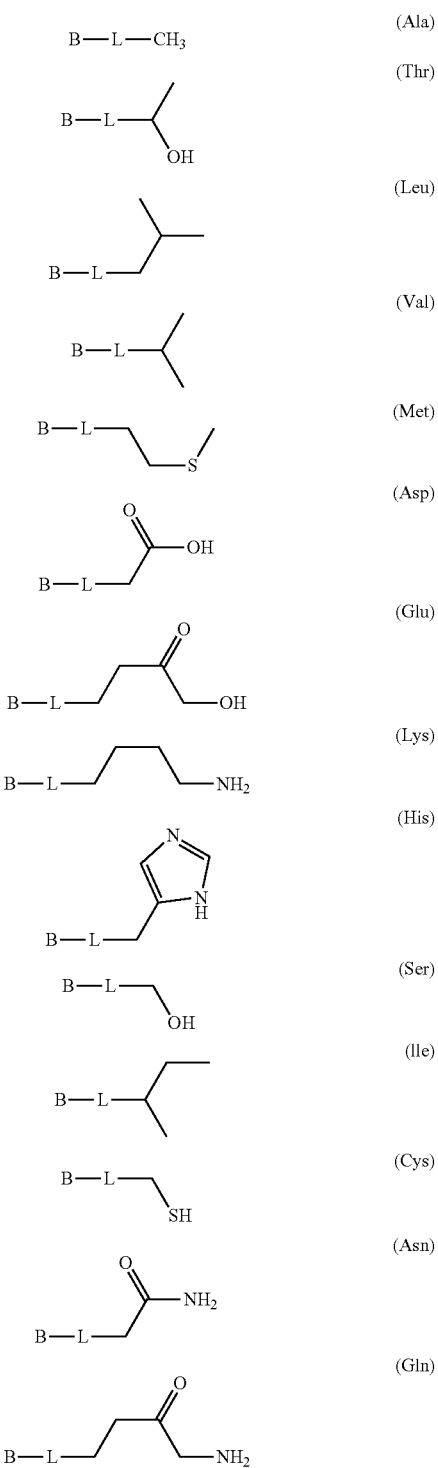

Alanine (Ala), Arginine (Arg), Asparagine (Asn), Aspartic Acid (Asp), Cysteine (Cys), Glutamic Acid (Glu), Glutamine (Gln), Glycine (Gly) (in other words, R is H), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), Valine (Val), Selenocysteine (Sec) and Pyrrolysine (Pyl).

For example, the moiety may be:

where B=base and Func=functional element, $R^E$ is H, optionally substituted $C_{1-10}$ alkyl, $C_{2-10}$ alkenyl, $C_{2-10}$ alkynyl and $C_{3-10}$ cycloalkyl groups, optionally substituted $C_{6-10}$ aryl, $C_{5-10}$ heteroaryl and $C_{3-10}$ heterocyclic groups.

In some embodiments L is preferably one of (24), (29), (30), (32), (33), (34), (35), (36) or an amino acid framework as described above, e.g. —CONCH---CO$_2$R$^E$ or —NCH---CO$_2$R$^E$.

Amino Acid Side Chain

In some preferred embodiments, the functional substituent Func is R, wherein R is an amino acid side chain. The linker may optionally be one of (24), (29), (30), (32), (33), (34), (35), (36) or an amino acid framework as described above, e.g. —CONCH---CO$_2$R$^E$ or —NCH---CO$_2$R$^E$.

Suitably, R is hydrogen or a natural or non-natural amino acid side chain. For example, natural amino acid side chains include the side chains of the 23 proteinogenic amino acids:

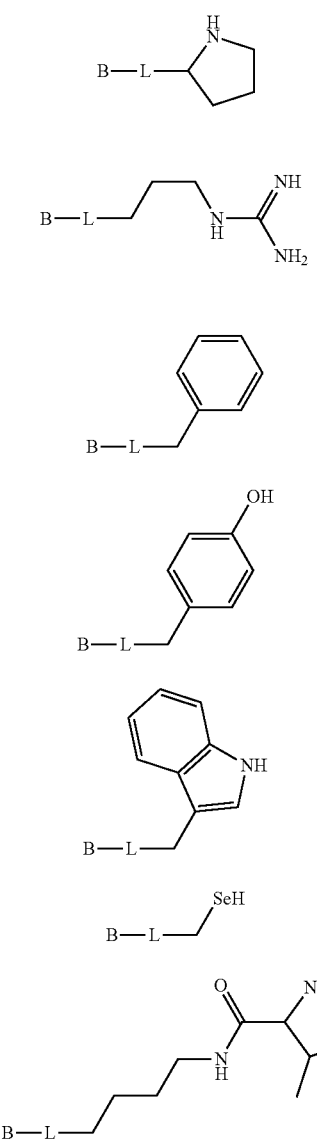
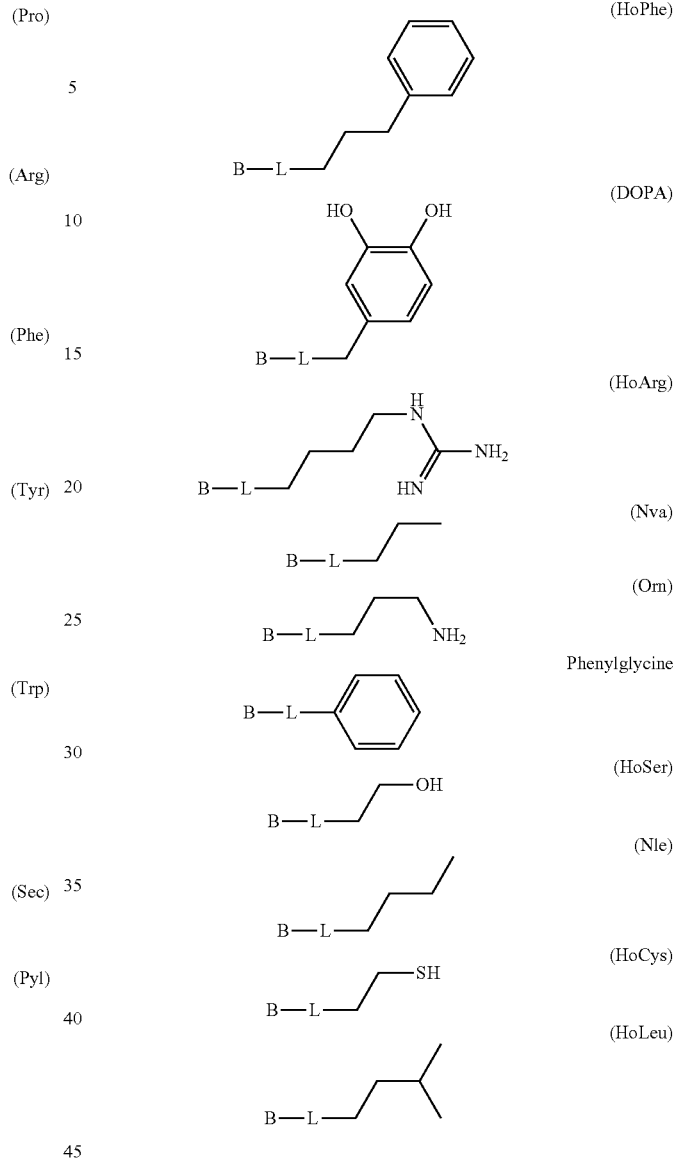

Especially preferred are histidine, serine, leucine, glutamic acid, lysine, phenylalanine, tyrosine and tryptophan. The amino acid side chain is optionally not hydrogen (glycine).

Non-natural amino acid side chains are known in the art. Non-natural amino acids may also be referred to as non-proteinogenic amino acids and include: Cit (citrulline), L-DOPA (L-3,4-dihydroxyphenylalanine), homoarginine, homocysteine, homoleucine, homophenylalanine, homoserine, Nle (norleucine), Nva (norvaline), Orn (ornithine), and phenylglycine.

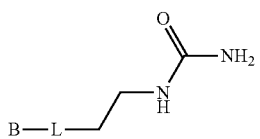

In some embodiments a functional sequence may have at least two, at least three, at least four, at least five, or more (e.g. one of 6, 7, 8, 9, 10, 11, 12, 13, 14 or 15), adjacent nucleotides each having a functional substituent that is an amino acid side chain (R). Each amino acid side chain may be independently selected from a natural or non-natural amino acid side chain, as described above.

In some embodiments, the amino acid side chain of adjacent nucleotides, optionally adjacent pyrimidine nucleotides or adjacent purine nucleotides, in the functional sequence is not the same. In some embodiments the amino acid side chain of adjacent nucleotides, optionally adjacent pyrimidine nucleotides or adjacent purine nucleotides, within a contiguous sequence of 3, 4, or 5 nucleotides (optionally a contiguous sequence of 3, 4, or 5 pyrimidine or purine nucleotides respectively) of the functional sequence is not the same.

In some embodiments the functional sequence comprises amino acid side chains of at least three of histidine, serine, leucine, glutamic acid, lysine, phenylalanine, tyrosine and tryptophan.

In some embodiments the functional sequence comprises two or more adjacent nucleotides having amino acid side chains that are different. In some embodiments the functional sequence comprises 3, 4, 5, 6, 7, 8, 9, 10, 11, 12, 13, 14, 15 or more adjacent nucleotides having amino acid side chains that are different.

In some embodiments the functional sequence comprises two or more adjacent nucleotides having amino acid side chains that are different and are independently selected from the group consisting of: histidine, serine, leucine, glutamic acid, lysine, phenylalanine, tyrosine and tryptophan.

In some embodiments the functional sequence comprises three or more adjacent nucleotides having amino acid side chains that are different and are independently selected from the group consisting of: histidine, serine, leucine, glutamic acid, lysine, phenylalanine, tyrosine and tryptophan.

In some embodiments the functional sequence comprises four or more adjacent nucleotides having amino acid side chains that are different and are independently selected from the group consisting of: histidine, serine, leucine, glutamic acid, lysine, phenylalanine, tyrosine and tryptophan.

In some embodiments the functional sequence comprises five or more adjacent nucleotides having amino acid side chains that are different and are independently selected from the group consisting of: histidine, serine, leucine, glutamic acid, lysine, phenylalanine, tyrosine and tryptophan.

Optional Substituents

As used herein, the term "optionally substituted" refers to a substituent that may be substituted with one or more (up to the maximum number of free valencies on that substituent) substituents. The substituents may be selected from:
—$C_{1-4}$alkyl,
—F, —Cl, —Br, —I
—$CF_3$, —$OCF_3$, —$SCF_3$,
—OH, —X—OH, —O—X—OH, —NH—X—OH, —$NR^S$—X—OH,
—$OC_{1-4}$alkyl, —X—$OC_{1-4}$alkyl, —O—X—$OC_{1-4}$alkyl, —NH—X—$OC_{1-4}$alkyl, —$NR^S$—X—O $C_{1-4}$alkyl,
—SH, —$SC_{1-4}$alkyl,
—CN,
—$NH_2$, —$NHC_{1-4}$alkyl, —$N(C_{1-4}$alkyl$)_2$,
—X—$NH_2$, —X—$NHC_{1-4}$alkyl, —X—$N(C_{1-4}$alkyl$)_2$,
—OC(O)$C_{1-4}$alkyl,
—C(O)OH, —C(O)O$C_{1-4}$alkyl,
—C(O)$C_{1-4}$alkyl,
—C(O)$NH_2$, —C(O)$NHC_{1-4}$alkyl, —C(O)N($C_{1-4}$alkyl$)_2$,
—NHC(O)$C_{1-4}$alkyl, —N($C_{1-4}$alkyl)C(O) $C_{1-4}$alkyl;
—$NHCONH_2$, —NH(CNH)$NH_2$. and
=O;
wherein each —X— is a bond or a $C_{1-4}$ alkylene and $R^S$ is —$C_{1-10}$alkyl, —$C_{2-10}$alkenyl, —$C_{2-10}$alkynyl, —$C_{6-10}$aryl, or —$C_{5-10}$heteroaryl.

In some embodiments, these optional substituents are selected from —$C_{1-4}$alkyl, —F, —Cl, —$CF_3$, —OH, —$OC_{1-4}$alkyl, —$NH_2$, —$NHC_{1-4}$alkyl, and —N($C_{1-4}$ alkyl$)_2$.

Attachment of the Functional Substituent

Attachment of the substituent may be at the 5-position of pyrimidine (e.g. C, T, U) or 7- or 8-position of purine (e.g. A, G), or may be by substitution of an amine outside a ring, substitution of 4-thiouridine, substitution of 5-halo pyrimidine, substitution of 5-bromo uracil, substitution of 5-iodo uracil. Attachment at the 5-position of pyrimidine may be preferred. Techniques for introducing a substituent at these positions are well known in the art, e.g. see Bioconjugate Techniques by Greg T. Hermanson Academic Press, July 2013, page 158; Spiridoula Matsika., Top Curr Chem (2015) 355:209-244. Techniques for attachment at the 7- or 8-position of purine are also well known in the art, e.g. see U.S. Pat. Nos. 8,759,502 B2 and 8,299,225 B2. Further substitutions are disclosed in U.S. Pat. No. 7,759,473 B2. Functional sequences according to the present invention may accommodate a wide range of substituent moieties at a wide range of attachment positions because polymerase compatibility is not required in the functional sequence.

In some embodiments at least two, or at least three or four, adjacent nucleotides in a contiguous sequence element of the functional sequence are modified by incorporation of such a substituent. In some embodiments one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 adjacent nucleotides in a contiguous sequence element of the functional sequence are modified by incorporation of such a substituent. In some embodiments each nucleotide in the functional sequence is modified by incorporation of such a substituent. In some embodiments each nucleotide in the functional sequence is modified by incorporation of such a substituent except for one of 1, 2, 3, 4, or 5 nucleotides.

For example, in some cases, the functional element comprises at least two adjacent modified nucleotides, such that the functional element comprises a dinucleotide of the following formula:

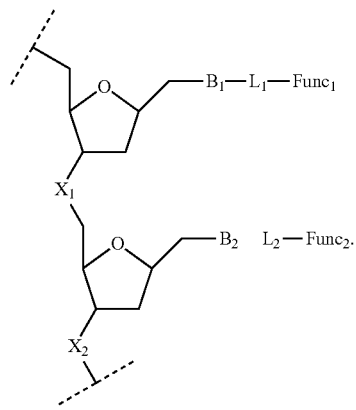

in which X represents the linkage, e.g. phosphodiester or phosphorothioate diester linkage, between nucleotides. The sugar residue illustrated may be modified or replaced with alternative sugar residues, cyclic or acyclic structures as described herein.

In some cases, the functional element comprises three adjacent nucleotides, such that the functional element comprises a trinucleotide of following formula:

in which X represents the linkage, e.g. phosphodiester or phosphorothioate diester linkage, between nucleotides. The sugar residue illustrated may be modified or replaced with alternative sugar residues, cyclic or acyclic structures as described herein.

Each group labelled 1, 2, 3 is independently selected from the options and preferred options for X, B, L, and Func.

In some embodiments, two, three or more or each pyrimidine nucleotide is modified by incorporation of such a substituent. In some embodiments, two, three or more or each purine nucleotide is modified by incorporation of such a substituent In some embodiments, two, three or more or each pyrimidine nucleotide is modified by incorporation of such a substituent, and purine nucleotides are not modified by incorporation of such a substituent.

In some embodiments, two, three or more or each purine nucleotide is modified by incorporation of such a substituent, and pyrimidine nucleotides are not modified by incorporation of such a substituent.

In other embodiments, one or more nucleotides (pyrimidine or purine) in the functional sequence are not modified by incorporation of such a substituent.

In some embodiments pyrimidine nucleotides are modified by incorporation of the substituent, not purine nucleotides. This may involve modification of all pyrimidines or selected pyrimidines. In some embodiments purine nucleotides are modified by incorporation of the substituent, not pyrimidine nucleotides. This may involve modification of all purines or selected purines. In some embodiments both pyrimidine and purine nucleotides are modified by incorporation of the substituent. This may involve modification of all pyrimidines and purines or selected pyrimidines and purines.

Functional sequences may therefore be prepared each having a different sequence structure, the sequence structure being a combination of base sequence and specific functional substituent associated with each base.

Purely by way of example a functional sequence may have the following sequence:

(1) $A_{Ala}G_{Glu}C_{Phe}U_{Thr}G_{Trp}C_{Asp}C_{Ser}A_{Val}U_{Lys}U_{His}G_{Glu}C_{Gly}U_{Tyr}$ [SEQ ID NO. 1]

or (2) $A_{Ala}G_{Glu}CUGC_{Asp}C_{Ser}A_{Val}U_{Lys}U_{His}G_{Glu}C_{Gly}U_{Tyr}$ [SEQ ID NO. 2]

In each of (1) and (2) R is the respective side chain of an amino acid indicated by the three letter code in sub-script. In (1) 13 adjacent nucleotides are modified with an amino acid side chain. In (2) an unmodified CUG triplet is present at positions 3-5.

The extent of functional substituent diversity is variable as desired and may be a product of how the coding table, and therefore the modified nucleotides are designed, selected and synthesised. In some embodiments each nucleotide of a functional sequence may contain a different functional substituent whereas in other embodiments the same modified nucleotide may appear more than once in a functional sequence, or different nucleotides within a functional sequence may be modified with the same functional substituent.

By providing functional sequences in which adjacent nucleotides each bear a functional substituent the functional sequence can present a high density of functional substituents (such as amino acid side chains) available for interaction with a target molecule.

Nucleotides of the functional sequence may contain other chemical modifications that do not alter the functional substituent, where present, or introduce such a substituent. These may include chemical substitution at a sugar position, a phosphate position, and/or a base position of the nucleic acid including, for example, incorporation of a modified nucleotide, conjugation to a high molecular weight, non-immunogenic compound (e.g. polyethylene glycol (PEG)), conjugation to a lipophilic compound, incorporation of a capping moiety (e.g. 3' capping, 5' capping, inverted dT 3'-3' capping), substitutions or modifications in the phosphate backbone, e.g. monothioate, dithioate, methyl phosphonate, alkyl phosphonate. Base modifications may include 5-position pyrimidine modifications, modifications at exocyclic amines, substitution of 4-thiouridine, substitution of 5-bromo- or 5-iodo-uracil, backbone modifications. Sugar modifications may include (deoxy)-ribose, 2'-amine nucleotides (2'-NH$_2$), 2'-fluoro nucleotides (2'-F), and 2'-O-methyl (2'-OMe) nucleotides.

Coding Element

A coding element may comprise, or consist of, a coding sequence. Optionally, the coding element may further comprise one, two or more fixed oligonucleotide sequences, as described below. A coding element is preferably an oligonucleotide molecule, although it may comprise non-nucleotide components, e.g. spacer or linker molecules.

The coding sequence may be a contiguous sequence of nucleotides that do not contain the modifications present in the functional sequence; preferably these are nucleotides comprising unmodified naturally occurring nucleosides (e.g. for RNA: adenosine, guanosine, 5-methyluridine, uridine, cytidine, and for DNA: deoxyadenosine, deoxyguanosine, thymidine, deoxyuridine, deoxycytidine) or containing modifications that permit the use of polymerase based amplification techniques. The modifications absent from the coding sequence are preferably functional substituents present on modified nucleotides of the functional sequence. They may be modifications to the base, e.g. inclusion of functional substituents as described in respect of the formula B-L-Func.

Preferably, the coding sequence does not contain the modifications present in the functional sequence in the sense that, and optionally to the extent that, the modifications absent from the coding sequence are those that would interfere with enzymatic amplification.

The base sequence of the coding sequence encodes the sequence structure, i.e. encodes the base sequence and specific modifications present on each respective corresponding nucleotide/nucleoside, of the functional sequence.

The coding sequence is amplifiable by routine techniques such as PCR, preferably without need to identify and use reverse transcriptase or polymerase enzymes capable of recognising or incorporating modified or non-naturally occurring nucleotides, and without the need to remove nucleotide modifications or otherwise chemically treat or modify the coding sequence prior to amplification.

The coding element may have one or two adjacent oligonucleotide sequence(s), e.g. one at the 5' and one at the 3' end of the coding sequence, thereby flanking the coding sequence. These sequences, each called herein a 'fixed coding sequence', preferably have a predetermined sequence (preferably non-random) allowing design and hybridisation of suitable primers for amplification of the coding sequence, e.g. during PCR. The coding sequence and fixed coding sequence preferably form a single contiguous oligonucleotide, called herein the coding element. As such, the coding element may comprise, or consist of, a coding sequence and one or more, preferably two, fixed sequences. The coding sequence may therefore be flanked by two fixed sequences which each form a contiguous oligonucleotide molecule with the coding sequence. Fixed coding sequences may be of any convenient length, usually 10 or more, or 15 or more, nucleotides, e.g. between 10 and 40 nucleotides, between 15 and 40 nucleotides or between 20 and 30 nucleotides.

The coding sequence is an oligomer of nucleotide n-mers, preferably a plurality of different n-mers or ab initio random sequence of n-mers, where n is an integer of 1 or greater, e.g. 1, 2, 3, 4, 5 or more. For example, a 2-mer is a di-nucleotide, e.g. AG, and a 3-mer is a tri-nucleotide, e.g. AGC. Each n-mer corresponds to a single nucleotide in the functional sequence, i.e. there is an n:1 correspondence between the number of nucleotides or bases in the coding sequence to the functional sequence. The sequence (i.e. the linear order or primary base sequence) of bases in the coding sequence may therefore be read and translated using a coding table to determine the sequence (i.e. linear order) of nucleotides, including the modifications incorporated in those nucleotides, present in the functional sequence.

As such, the coding sequence has n times the number of nucleotides as the functional sequence and the length of the coding sequence will normally be n times that of the functional sequence. For example, the coding sequence may have the same number of nucleotides or bases as the functional sequence (n=1), or may have twice as many (n=2), three times as many (n=3), four times as many (n=4) or five times as many (n=5), etc.

In preferred embodiments the value of n is at least 2, e.g. one of 2, 3, 4, or 5.

In some embodiments the coding element additionally comprises an oligonucleotide sequence (preferably a sequence of non-modified nucleotides) unique to the coding element. This may be a "coding table ID sequence" and may be positioned in-between one of the fixed coding sequences and the coding sequence. The coding table ID sequence may be used to assign a coding table used in synthesis of a given oligonucleotide construct. When olignucleotide construct libraries are used, or are mixed for use, the coding table ID sequence allows the correct coding table to be assigned to oligonucleotide constructs within, or selected from, the libraries, thereby allowing the sequence of the functional sequence to be decoded. The length of the coding table ID sequence may be any one or 1, 2, 3, 4, 5 or more nucleotides, preferably 1 to 3 or 1 or 2 nucleotides.

Nucleoside, Nucleotide

The term "nucleotide" refers to a compound containing a nucleoside or a modified nucleoside and at least one phosphate group or a modified phosphate group linked to it by a covalent bond. Exemplary covalent bonds include, without limitation, an ester bond between the 3', 2' or 5' hydroxyl group of a nucleoside and a phosphate group.

The term "oligonucleotide" refers to a compound containing two or more nucleotides joined together in a polymeric chain. Oligonucleotides may be deoxyribonucleic acids or ribonucleic acids. Oligonucleotides may be single stranded or double stranded.

Modified nucleotides and oligonucleotides of the present invention may include chemical modifications as described herein such as a chemical substitution at a sugar position, a phosphate position, and/or a base position of the nucleic acid including, for example., incorporation of a modified nucleotide, incorporation of a capping moiety (e.g. 3' capping), conjugation to a high molecular weight, non-immunogenic compound (e.g. polyethylene glycol (PEG)), conjugation to a low molecular weight compound (e.g. cholesterol), conjugation to a peptide (e.g. a cell-penetrating peptide), substitutions in the phosphate group (e.g. phosphorothioate). Base modifications may include 5-position pyrimidine modifications, modifications at exocyclic amines, substitution of 4-thiouridine, substitution of 5-bromo- or 5-iodouracil, backbone modifications. Sugar modifications may include 2'-amino nucleotides (2'-$NH_2$), 2'-fluoro nucleotides (2'-F), 2'-O-methyl (2'-OMe) nucleotides, 2'-O-allyl nucleotides, 2'-O-β-methoxyethyl nucleotides, "locked" nucleotides (e.g. LNA) or tricyclo-DNA nucleotides. The bonds between the central phosphorus atom of a phosphate and the, or each, nucleoside are suitably via oxygen, that is, the 3' and or 5' end of the nucleoside is an alcohol. However, nucleoside analogues in which the 3' and or 5' end of the nucleoside is not an alcohol, but rather a suitable analogue, are also envisaged. For example, the 3' and/or 5' end of a nucleoside may be a thiol, a selenol, or an amine.

The term "nucleoside" refers to a compound containing a sugar part and a nucleobase, e.g. pyrimidine or purine base. Exemplary sugars include, without limitation, ribose, 2-deoxyribose, arabinose and the like. Exemplary nucleobases include, without limitation, thymine, uracil, cytosine, adenine, guanine, purine, hypoxanthine, xanthine, 2-aminopurine, 2,6-diaminopurine, 5-methylcytosine, 4-fluorouracil, 5-chlorouracil, 5-bromouracil, 5-iodouracil, 5-trifluoromethyluracil, 5-fluorocytosine, 5-chlorocytosine, 5-bromocytosine, 5-iodocytosine, 5-propynyluracil, 5-propynylcytosine, 7-deazaadenine, 7-deazaguanine, 7-deaza-8-azaadenine, 7-deaza-8-azaguanine, isocytosine, isoguanine and the like.

The term "nucleoside analogues" as used herein refers to a modified nucleoside in which the sugar part is replaced with any other cyclic or acyclic structure. Exemplary nucleoside analogues in which the sugar part is replaced with another cyclic structure include, without limitation, monomeric units of morpholinos (PMO) and tricyclo-DNA.

Exemplary nucleoside analogues in which the sugar part is replaced with an acyclic structure include, without limitation, monomeric units of peptide nucleic acids (PNA) and glycerol nucleic acids (GNA). Oligonucleotides may be synthesised having a functional element or functional sequence comprised of peptide nucleic acids where nucleosides are linked by a peptide bond in place of the conventional phosphodiester bond. The sugar of the nucleoside may be replaced with N(-2-aminoethyl)-glycine units, which may optionally each be linked to a pyrimidine or purine base by a methylene bridge and carbonyl group (e.g. see Shakeel et al. Peptide nucleic acid (PNA)—a review. Journal of Chemical Technology and Biotechnology (June 2006)).

The term "nucleoside analogue" additionally refers to a nucleoside any part of which is replaced by a chemical group of any nature. Exemplary nucleoside analogues include, without limitation, 2'-substituted nucleosides such as 2'-fluoro, 2-deoxy, 2'-O-methyl, 2'-O-β-methoxyethyl, 2'-O-allylriboribonucleosides, 2'-amino, locked nucleic acid (LNA) monomers and the like.

Suitably, nucleoside analogues may include nucleoside analogues in which the sugar part is replaced by a morpholine ring as depicted below.

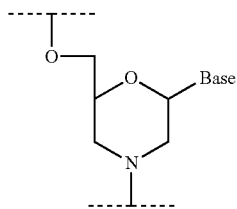

In structures of this type, it will be appreciated that the labels 3' and 5', as applied to conventional sugar chemistry, apply by analogy. That is, in the structure depicted, the hydroxylmethyl substituent on the ring is considered the 5' end, while the third nitrogen valency is considered the 3' end.

The term "oligonucleotide analogue" as used herein refers to a modified oligonucleotide, which is chemically modified at either its phosphate groups or has its nucleosides replaced by nucleoside analogues. Exemplary oligonucleotide analogues include, without limitation, phosphorothioate oligonucleotides (PS), phosphorodiamidate morpholino oligonucleotides (morpholinos, PMO), tricyclo-DNA.

The term "phosphate group" as used herein refers to phosphoric acid $H_3PO_4$ wherein any hydrogen atoms are replaced by one, two or three organic radicals to give a phosphoester, phosphodiester, or phosphotriester, respectively. Oligonucleotides may be linked by phosphodiester, phosphorothioate or phosphorodithioate linkages.

Coding Table

Preparation of a given oligonucleotide construct is conducted in accordance with a coding table that describes the relationship between each nucleotide added to the functional sequence and the n-mer added to the coding sequence at a corresponding position.

The coding table may be provided in the form of a table, database, datasheet, chart or similar. It may be provided in physical form, e.g. on paper, or in electronic form, e.g. stored on a computer readable medium, in an email or accessible via the internet.

In principle a coding table may describe $4^n$ different n-mers and will indicate the sequence structure (at least base and its functional substituent) of the nucleotide or nucleoside encoded by the n-mer. Examples of a coding table for constructs according to the present invention are shown in FIGS. 11A and 12A for n=2 and n=3 respectively.

In FIG. 11A, bases of 4 kinds are arranged transversely (5' direction) in the order A, C, G and T and bases of 4 kinds are arranged longitudinally (3' direction) in the order A, C, G and T thereby providing 16 combinations (for n=2) represented by the boxes shown. A base is read from the 5' side and then the 3' side to form the coding sequence dinucleotide. For example, in FIG. 11A the dinucleotide CA in the coding sequence corresponds to $C_{Phe}$ (Cytosine modified by inclusion of an amino acid side chain of Phenylalanine) in the functional sequence.

The coding tables illustrated in FIGS. 11A and 12A are purely by way of example, in principle any desired modified nucleotide can be encoded by a selected n-mer.

Whilst nucleotides of the functional sequence preferably contain nucleotides modified to incorporate a functional substituent, nucleotides outside the functional sequence, e.g. in the fixed functional sequence(s) of the functional element and in nucleotide sequences of the coding sequence, preferably are not modified to incorporate such a functional substituent. These sequences may contain unmodified nucleotides, i.e. naturally occurring nucleotides or may contain other chemical modifications, preferably modifications that do not prevent the use of polymerase amplification techniques. Such modifications may include chemical substitution at a sugar position, a phosphate position, and/or a base position of the nucleic acid including, for example, incorporation of a modified nucleotide, incorporation of a capping moiety (e.g. 3' capping, 5' capping, inverted dT 3'-3' capping), substitutions or modifications in the phosphate backbone, e.g. monothioate, dithioate, methyl phosphonate, alkyl phosphonate. Base modifications may include 5-position pyrimidine modifications, modifications at exocyclic amines, substitution of 4-thiouridine, substitution of 5-bromo- or 5-iodo-uracil, backbone modifications. Sugar modifications may include (deoxy)-ribose, 2'-amine nucleotides (2'-NH$_2$), 2'-fluoro nucleotides (2'-F), and 2'-O-methyl (2'-OMe) nucleotides.

Oligonucleotide Construct Comprising a Support Matrix

In some embodiments each of the functional element and coding element are attached to a support matrix, respectively. In some embodiments the support matrix may have attached a single coding element and a single functional element. The coding sequence of the coding element provides a label for each support matrix allowing the sequence structure of the functional sequence(s) of the functional elements attached to the support matrix to be determined in a 1-to-1 manner.

In some embodiments the number of coding elements attached to the support matrix is the same as the number of functional elements attached to the support matrix. In some embodiments the number of attached coding elements is less than the number of attached functional elements. Optionally, only a single coding element is attached. In some embodiments the support matrix may comprise one or a plurality of functional elements and only one coding element.

In some embodiments each functional element attached to a single support matrix is identical or contains the same functional sequence, and preferably each coding element attached to a single support matrix is identical or contains the same coding sequence. The coding sequence(s) attached to the support matrix encode the functional sequence(s) attached to the same support matrix. By providing a plurality of support matrices each attached to a different oligonucleotide construct a library of oligonucleotide constructs may be provided.

A support matrix may comprise material which is stiff, rigid, malleable, solid, porous or non-porous. It may comprise a solid material, or a semi-solid, gel, etc material. For example, the material from which the support matrix is made may comprise plastic, glass, biologically inert metals such as titanium, ceramic, silicone, gelatin, dextran, cellulose, hydroxylated methacrylate, polystyrene, or collagen.

In some embodiments support matrices may be particles, microcarriers or beads to which an oligonucleotide may be attached. The particle, microcarrier or bead may be of any shape or configuration, but may preferably be spherical or rod shaped. In some embodiments a particle may comprise a microcarrier, as described in the IUPAC Compendium of Chemical Terminology (2nd Edition, 1992, Vol. 64, p. 160). Particles of various shapes are known in the art and include, for example, beads of various kinds.

Embodiments of particles include microbeads, such as agarose beads, polyacrylamide beads, silica gel beads. The particles may comprise cellulose, or a derivative, such as DEAE-cellulose, modified hydrophilic beads and carbon based microcarriers. The particle may comprise a resin suitable for use as a chromatography matrix, such as an anion exchange resin.

Particles, beads or microcarriers may comprise a cellulose microcarrier (e.g. DE-52 (Whatman), DE-53 (Whatman), QA-52 (Whatman)), hydrophilic microcarrier, a hydroxylated methacrylic matrix microcarrier or derivatised hydrophilic beaded microcarrier, TSKgel Tresyl-5Pw (Tosoh), Toyopearl AF-Tresyl-650 (Tosoh) macroporous or microporous microcarrier, SM1010 (Blue Membranes) SH1010 (Blue Membranes), dextran based microcarrier, Cytodex 1 (GE Healthcare), Cytodex 3 (GE Healthcare), a polystyrene based microcarrier, e.g. Hillex or Hillex II (SoloHill Engineering, Inc.).

Cytodex 1 is based on a cross-linked dextran matrix which is substituted with positively charged N, N-diethylaminoethyl groups. The charged groups are distributed throughout the microcarrier matrix. Cytodex 3 consists of a thin layer of denatured collagen chemically coupled to a matrix of cross-linked dextran. Hillex and Hillex II are modified polystyrene microcarriers having a cationic trimethyl ammonium coating.

Beads or microbeads suitable for use include those which are used for gel chromatography, for example, gel filtration media such as Sephadex. Suitable microbeads of this sort include Sephadex G-10 having a bead size of 40-120 µm (Sigma Aldrich catalogue number 27,103-9), Sephadex G-15 having a bead size of 40-120 µm (Sigma Aldrich catalogue number 27,104-7), Sephadex G-25 having a bead size of 20-50 µm (Sigma Aldrich catalogue number 27,106-3), Sephadex G-25 having a bead size of 20-80 µm (Sigma Aldrich catalogue number 27,107-1), Sephadex G-25 having a bead size of 50-150 µm (Sigma Aldrich catalogue number 27,109-8), Sephadex G-25 having a bead size of 100-300 µm (Sigma Aldrich catalogue number 27,110-1), Sephadex G-50 having a bead size of 20-50 µm (Sigma Aldrich catalogue number 27,112-8), Sephadex G-50 having a bead size of 20-80 µm (Sigma Aldrich catalogue number 27,113-6), Sephadex G-50 having a bead size of 50-150 µm (Sigma Aldrich catalogue number 27,114-4), Sephadex G-50 having a bead size of 100-300 µm (Sigma Aldrich catalogue number 27,115-2), Sephadex G-75 having a bead size of 20-50 µm (Sigma Aldrich catalogue number 27,116-0), Sephadex G-75 having a bead size of 40-120 µm (Sigma Aldrich catalogue number 27,117-9), Sephadex G-100 having a bead size of 20-50 µm (Sigma Aldrich catalogue number 27,118-7), Sephadex G-100 having a bead size of 40-120 µm (Sigma Aldrich catalogue number 27,119-5), Sephadex G-150 having a bead size of 40-120 µm (Sigma Aldrich catalogue number 27,121-7), and Sephadex G-200 having a bead size of 40-120 µm (Sigma Aldrich catalogue number 27,123-3).

Sepharose beads, for example, as used in liquid chromatography, may also be used. Examples are Q-Sepharose, S-Sepharose and SP-Sepharose beads, available for example from Amersham Biosciences Europe GmbH (Freiburg, Germany) as Q Sepharose XL (catalogue number 17-5072-01), Q Sepharose XL (catalogue number 17-5072-04), Q Sepharose XL (catalogue number 17-5072-60), SP Sepharose XL (catalogue number 17-5073-01), SP Sepharose XL (catalogue number 17-5073-04) and SP Sepharose XL (catalogue number 117-5073-60).

In other embodiments a support matrix may be formed by a well or address on an array.

Arrays typically comprise a plurality of different, known, and usually predetermined, locations or addresses at which a specific molecule may be located. Such arrays, also described as "microarrays", "chips", or "slides" have been generally described in the art, for example, U.S. Ser. No. 09/536,841, WO 00/58516, U.S. Pat. Nos. 5,143,854, 5,445,934, 5,744,305, 5,677,195, 6,040,193, 5,424,186 and Fodor et al, Science, 251:767-777 (1991), each of which is incorporated by reference in its entirety.

Arrays may generally be produced using mechanical synthesis methods or light directed synthesis methods that incorporate a combination of photolithographic methods and solid phase synthesis methods. Techniques for the synthesis of these arrays using mechanical synthesis methods are described in, e.g. see U.S. Pat. Nos. 5,384,261, 6,121,048, and 6,040,193, which are incorporated herein by reference in their entirety.

Whilst a planar array surface may be preferred, the array may be fabricated on a surface of virtually any shape or even a multiplicity of surfaces. Arrays may be oligonucleotides on beads, gels, polymeric surfaces, fibers, glass, plastics, slides or any other appropriate substrate, e.g see U.S. Pat. Nos. 5,770,358, 5,789,162, 5,708,153, 6,040,193 and 5,800,992, which are hereby incorporated by reference in their entirety.

Locations or addresses may be formed by depositing or printing material at selected positions on the array. Locations or arrays may also be formed by physical design of the array, e.g. in the form of wells or microwells.

Arrays may be packaged in such a manner as to allow for diagnostics or can be an all-inclusive device; e.g., U.S. Pat. Nos. 5,856,174 and 5,922,591 incorporated in their entirety by reference.

In some embodiments an array may comprise a support, preferably solid, having a plurality of addresses. Each address may have one or a plurality of functional elements attached to the support and one or a plurality of coding elements attached to the support (the coding element encoding the sequence structure of the functional sequence of the functional element) or may have attached one or a plurality of single molecules that comprise both the functional element and coding element. Each address preferably has a different pair of functional and coding elements attached, or different single molecule that comprises both the functional element and coding element, thereby providing a library of different functional sequences across the plurality of addresses. As such an array may have $10^1$ $10^2$, $10^3$, $10^4$, $10^5$, $10^6$, $10^7$, $10^8$, $10^9$, $10^{10}$, or more, different oligonucleotide constructs attached to it at a corresponding number of addresses.

Attachment of oligonucleotides to a support matrix may be direct or indirect, covalent or non-covalent. For example, attachment may be via a cleavable linker which does not affect the oligonucleotide or the protection groups used during synthesis. Examples include a disulfide linker (cleavable by TCEP (Tris(2-carboxyethyl)phosphine hydrochloride)), a sulfone linker (cleavable by hindered base such as DBU (1,8-Diazabicyclo [5.4.0]undec-7-ene)) or a photocleavable linker (cleavable by UV light).

Oligonucleotide Construct Library

A library of oligonucleotide constructs may be prepared by a 'split synthesis' process. Split synthesis is a technique suitable for generation of one-bead one-oligonucleotide libraries where each bead presents one or more copies of a single oligonucleotide sequence or species (see Yang X, et al. Construction and selection of bead bound combinatorial oligonucleoside phosphorothioate and phosphorodithioate aptamer libraries designed for rapid PCR-based sequencing. *Nucleic Acids Research* 30 (2002) e123; Yang X, et al. Immunofluorescence assay and flow cytometry selection of bead-bound aptamers. *Nucleic Acids Research* 31(10) (2003) e54; Gorenstein D G, et al. Bead Bound Combinatorial Oligonucleoside Phosphorothioate and Phosphorodithioate Aptamer Libraries and U.S. Pat. No. 7,338,762).

In one embodiment, copies of a single oligonucleotide are introduced onto each bead or other solid support capable of supporting DNA synthesis (e.g. made of controlled pore glass (CPG) or a polymer) by a 'mix and separate' split synthesis method. Oligonucleotides are synthesised by conventional phosphoramidite synthesis using a DNA or RNA synthesiser in step-wise fashion on a linker moiety, as described above, covalently attached to the support matrix, e.g. a polystyrene bead, and optionally with a spacer such as non-cleavable hexaethyleneglycol or polyT (e.g. TTTT) attached to the first phosphoramidite. Use of a linker enables the synthesized oligonucleotide to remain covalently attached to the support matrix after full base and phosphate ester deprotection. The oligonucleotide chain is thereby extended in a 3' to 5' direction away from the bead.

For example, a "Library on Support" may be prepared as follows:
1. Prepare solid support resin having free hydroxide residue on its surface.
2. Conjugate several thymidine to free hydroxyl residues on the solid support as spacer, if necessary.
3. Competitively conjugate DMT-protected thymidine and Lev-protected thymidine to the solid support or spacer on the solid support using phosphoramidite chemistry.
4. Start extension of two oligonucleotides using selective deprotection of DMT and Lev groups A "Library in Solution" may be prepared as follows:
1. Prepare solid support resin having free hydroxide residue on its surface.
2. Conjugate cleavable linker moiety to the solid support using e.g. phosphoramidite chemistry. In some embodiments, non-cleavable spacer, e.g. four repeat of native thymidine, is inserted between solid support and cleavable linker moiety to avoid steric hindrance of functional element and target molecule.
3. Conjugate a chemical compound having both DMT group and Lev group to provide a branching moiety (indicated in FIG. 3).
4. Start extension of two oligonucleotides using selective deprotection of DMT and Lev groups.

In either case, the first step may involve synthesizing the fixed sequence located between the solid support and the functional sequence in the functional element or coding sequence in the coding element using differential removal of DMT or Lev and phosphoramidite oligonucleotide extension for relevant oligonucleotide constructs. The coding table ID sequence may be formed in the coding element at this time.

Differential removal of DMT or Lev is achieved using different deblocking reactions. Example of such differential deblocking reactions are achieved by for example but not limited to, 3% trichloroacetic acid in dichloromethane to deblock DMT group and 0.5M diamine in pyridine/acetic acid mixture (1:1) to deblock Lev group. To apply differential removal scheme to oligonucleotide synthesis, proper exo-cyclic amine protection groups selected from groups durable in said differential deblocking reactions is also important. Examples of such protection group are indicated below but are not limited to those shown.

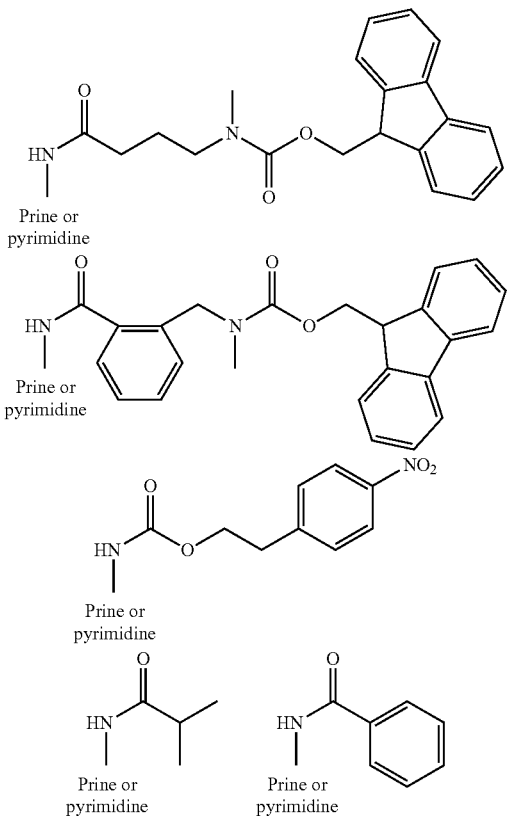

To form the functional and coding sequences the solid supports, having fixed sequences already formed, may be split into equal volume of $2^x$ parts, where x is the number n-mers in the coding table. Each split-batch of solid supports is separately treated to extend the functional sequence by one nucleotide and to extend the coding sequence by n nucleotides by selecting the appropriate n-mer from the coding table to correspond with the nucleotide added to the functional sequence. The split-batches treated for extension are then mixed and the process repeated until all of necessary extension reactions in the functional sequence and coding sequence have been completed, e.g. see FIGS. 8 and 9.

The remaining fixed sequences may then be synthesized in accordance with the process described above for the first step.

The process may commence with extension of either the functional or coding sequence and may apply the same number of extension steps to each of the functional and coding sequence. The step wise extension is controlled by use of different protecting groups for each of the functional and coding elements respectively. Suitable protecting groups include levulinoyl (4-oxopentanoic acid, Lev) or its ester and dimethoxytrityl (DMT).

When forming the coding sequence, addition of the n-mer may involve addition of a pre-formed di-, tri-, tetra- or penta-nucleotide as appropriate but in preferred embodiments the n-mer may be added by addition of n monomers, each selected so as to form the desired n-mer in situ in the coding sequence. This may require performance of n extension reactions of the coding sequence for each extension reaction of the functional sequence, which reactions may be appropriately controlled by control of the chemical (de) protection conditions.

Chemical protection refers to compound(s) in which one or more reactive functional groups are protected from undesirable chemical reactions under specified conditions (e.g., reagents, solvents, pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Greene's Protective Groups in Organic Synthesis (P. Wuts; 5th Edition; John Wiley and Sons, 2014).

Unless otherwise specified, a reference to a particular compound also includes chemically protected forms thereof.

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O●).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Extension of the functional sequence may begin and optionally end with addition of nucleotides that do not contain a functional substituent, as described herein, in a defined, optionally complementary, sequence (e.g. forming the fixed functional sequence). This may enable them to be used as primers for polymerase based amplification or to hybridise and form a stem-loop structure contributing to conformational stability of the functional sequence. When forming the functional sequence one or more, preferably two or more, modified nucleotides incorporating a functional substituent, as described herein, are included in the functional sequence. The resulting functional sequence preferably includes at least two, or at least three, adjacent nucleotides each incorporating a functional substituent, as described herein.

When synthesising the coding sequence, for each addition of 1 nucleotide to the functional sequence the coding sequence is extended by addition of one n-mer, where n is at least 1, preferably at least 2 (e.g. one of 2, 3, 4, or 5), to produce a coding sequence that is n times the length of the functional sequence. Each n-mer added to the coding sequence is selected to encode the corresponding nucleotide on the functional sequence, e.g. according to a coding table. As described above, addition of one n-mer may be achieved not only by using a n-mer phosphoramidite but also by using n monomer phosphoramidite reactions. This approach is favourable because it provides for flexible production of an oligonucleotide construct library having a wide range of functional sequences and corresponding coding sequences.

In some embodiment, more than one Library on Support or Library in Solution, are separately prepared each based on different coding tables, the libraries are then mixed to form a mixed library having a greater variety of functional sequences. The coding table ID sequences inserted in each coding element may be used to identify and select the correct coding table in order to translate a given coding sequence into the sequence structure of the associated functional sequence.

Optionally, one or more or each of the fixed functional sequence(s) and fixed coding sequence(s) may be added en bloc, by addition of a respective pre-prepared sequence and not requiring step wise addition to build the fixed sequence element. This may reflect the fact that the fixed sequences may be the same between oligonucleotide constructs, the constructs differing in the sequence of the functional sequence and related coding sequence. To perform the addition of an oligonucleotide en bloc, de novo synthesized oligonucleotides are fully deprotected and hybridized with separately synthesized native oligonucleotides complementary with the relevant fixed sequence to form sticky- or blunt-ends. A sticky-end complementary oligonucleotide is preferable to allow proper location of added oligonucleotides. A DNA ligase is then used to make a phosphodiester bond between the two oligonucleotides.

When synthesising the functional and coding sequences, incorporation of nucleotides that do not contain a functional substituent may include non-modified nucleotides or modified nucleotides that permit polymerase based amplification, e.g. by PCR.

To generate a combinatorial library of oligonucleotide constructs a 'split and mix' process may be used (FIG. 8), and in particular may be applied during synthesis of the functional sequence and coding sequence. A plurality of synthesis reactions, e.g. 16, are conducted separately to add a first nucleotide to the functional sequence and first n-mer to the coding sequence for a plurality of different oligonucleotide constructs, the first nucleotide and n-mer being different between each construct (FIG. 8). The support matrices (having nascent constructs attached) are then mixed (FIG. 9A) and then split into a plurality of groups (e.g. 16) which are the subject of the next synthesis step, i.e. addition of the next nucleotide to the functional sequence and next n-mer to the coding sequence. The cycle of synthesis, mixing, and splitting is repeated as many times as necessary to produce a functional sequence of the required length.

The process allows generation of large numbers of different oligonucleotide constructs of the order of $a^b$ where a is the number of groups of synthesis reactions (e.g. number of columns in FIG. 9A) and b is the number of rounds of synthesis (or the length of the functional sequence). Where 16 groups are used a library of more than $10^{12}$ oligonucleotide constructs, one per support matrix, each having a different functional sequence (of length b nucleotides) can be created in only 10 cycles.

In preferred embodiments a library of oligonucleotide constructs may be conveniently prepared by synthesis of oligonucleotide constructs on particles, microcarriers or beads, e.g. polystyrene beads. The library may be used for selection of effective functional sequences against a target molecule. Because each particle, microcarrier or bead of the library may contain hundreds or thousands of copies of a single oligonucleotide construct (or functional sequence) it may capture sufficient target molecule to be selectable in a single cycle. Such capture may be monitored by particle sorting equipment, e.g. by monitoring fluorescence intensity of a fluorescent dye conjugated with the target molecule. Since hundreds of thousands of interactions can be monitored, the difference in fluorescence intensity between particles will reflect statistical differences of interaction between the target molecule and the oligonucleotide construct on each particle. As such, the approach described avoids the need for iterative rounds of solution enrichment and amplification of potential binding agents, such as that required by SELEX, and so can be completed much faster, often in one or two cycles.

Oligonucleotide constructs of the present invention also permit identification of target selected oligonucleotides by polymerase based amplification techniques, e.g. PCR, because the coding sequence is designed to be suitable for such amplification and encodes the precise sequence structure of the functional sequence.

Accordingly, a method of preparing an oligonucleotide construct is provided, the oligonucleotide construct comprising a functional sequence and a coding sequence, the method comprising:
 (i) extension of said functional sequence by addition of a single modified nucleotide,
 (ii) extension of said coding sequence by addition of a nucleotide n-mer, the n-mer selected to encode the structure of said modified nucleotide of step (i), wherein n is an integer of 1 or greater and the n-mer does not contain the (or a) modification of said modified nucleotide of step (i),
wherein either step (i) or (ii) may be performed first and steps (i) and (ii) are performed sequentially.

Steps (i) and (ii) may be performed a plurality of times to generate a functional sequence of desired length, e.g. one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides, and a coding sequence having a length n times that of the functional sequence, where n is preferably one of 2, 3, 4, or 5.

Oligonucleotide constructs may be prepared attached to a plurality of solid supports, e.g. particles, beads or microcarriers as described herein. A library of different oligonucleotide constructs attached to solid supports may be prepared. The functional sequence may form part of an oligonucleotide functional element and the coding sequence may form part of an oligonucleotide coding element. The functional element and coding element may be separately attached to the, or each, solid support(s) and may be extended from separate oligonucleotide linker moieties attached to the solid support(s). Alternatively, the functional element and coding element may be extended from a branch moiety, wherein the branch moiety is attached to the solid support, e.g. via a linker or spacer moiety. The branch moiety may be suitable to allow extension of two oligonucleotides, i.e. the functional and coding elements, to form a V- or Y-structure. The method may therefore comprise alternate extension of each branch.

Preparation of the library of solid supports may follow a split and mix synthesis and may be in accordance with a coding table that describes the relationship between each nucleotide added to the functional sequence and the n-mer added to the coding sequence at a corresponding position. Each performance of steps (i) and (ii) [in either order] forms a round of extension. Between rounds of extension the solid supports are mixed and then divided into $2^x$ parts where x is the number of n-mers in the coding table. At least one, preferably each, of the $2^x$ parts is then used as the basis of a further round of extension, This split and mix process may be repeated until all of the extension reactions necessary to form the functional and coding sequences have been completed. Several rounds of extension may be performed, as desired, in order to form oligonucleotide constructs having the desired length of functional and coding sequences.

Once synthesis is complete, the solid supports may be recovered and combined to form a library. The library may be subjected to screening or other assays, e.g. as described herein.

Functional Screening

Oligonucleotide constructs may be screened or assayed to identify or select one or more constructs having desired physical, chemical or functional properties. Preferably, such methods are performed in vitro. In some preferred embodiments they may be screened or assayed to identify an oligonucleotide construct capable of binding a target molecule, preferably with high affinity and/or with high specificity.

In some embodiments a method is provided for identifying an oligonucleotide construct(s) (or functional sequence) having affinity for a target molecule, the method comprising contacting a mixture of different oligonucleotide constructs with a target molecule under conditions that permit the oligonucleotide construct and target molecule to bind and form an oligonucleotide construct:target molecule complex, and partitioning the complexes from unbound oligonucleotides and/or unbound target molecule.

In this specification the term "partition" refers to separation or removal of one or more molecular species, complexes or conjugates. The partitioning step may separate oligonucleotide construct:target molecule complexes from free oligonucleotide constructs. Partitioning may involve immobilization of oligonucleotide construct:target molecule complexes on a solid support thereby separating and purifying the complexes from non-immobilised molecular species. Partitioning may also involve separation of complexes from unwanted contaminants.

The conditions under which the mixture of different oligonucleotide constructs are contacted with a target molecule may be varied to promote complex formation or dissociation and thereby select for oligonucleotide constructs having lower or higher affinity for the target molecule. Similarly, selection of oligonucleotide constructs having greater relative selectivity for the target molecule may be enhanced by varying the selection condition, e.g. by removing oligonucleotides that bind to a structurally similar but non-identical molecule to the target molecule by challenging the mixture with such a molecule. Oligonucleotide constructs may be identified having high affinity ($K_d$) for a target molecule of 10 µM or less, and preferably one of 1 µM or less, 500 nM or less, 100 nM or less, 50 nM or less, 1 nM or less, or 500 pM or less.

A target molecule may be any molecule, compound, ion or salt of interest, e.g. a protein, lipoprotein, glycoprotein, polypeptide, peptide, carbohydrate, polysaccharide, lipopolysaccharide, fat, lipid, nucleic acid, metabolite, small molecule, drug or dye. In some embodiments the target molecule may be replaced by a macromolecule, complex of molecules, cell, tissue or virus. By way of example, a protein or peptide target may be a receptor, enzyme, protein kinase, cytokine, antibody or growth factor. Target molecules may be isolated or purified.

A target molecule may be immobilised on a solid support. A solid support refers to any substrate having a surface to which molecules may be attached, directly or indirectly, through either covalent or non-covalent bonds. The solid support may include any substrate material that is capable of providing physical support for the target molecules that are attached to the surface. The material is generally capable of enduring conditions related to the attachment of the target molecules to the surface and any subsequent treatment, handling, or processing encountered during use.

The materials may be naturally occurring, synthetic, or a modification of a naturally occurring material. Suitable solid support materials may include silicon, graphite, mirrored surfaces, laminates, ceramics, plastics (including polymers such as, e.g., poly(vinyl chloride), cyclo-olefin copolymers, agarose gels, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver.

Additional rigid materials may be considered, such as glass, which includes silica and further includes, for example, glass that is available as Bioglass. Other materials that may be employed include porous materials, such as, for example, controlled pore glass beads, crosslinked beaded sepharose or agarose resins, or copolymers of crosslinked bisacrylamide and azalactone. Any other materials known in the art that are capable of having one or more functional groups, such as any of an amino, carboxyl, thiol, or hydroxyl functional group, for example, incorporated on its surface, are also contemplated.

The material used for a solid support may take any of a variety of configurations ranging from simple to complex. The solid support can have any one of a number of shapes, including a strip, plate, disk, rod, particle, bead, tube, well, or column. The solid support may be porous or non-porous, magnetic, paramagnetic, or non-magnetic, polydisperse or monodisperse, hydrophilic or hydrophobic. The solid support may also be in the form of a gel or slurry of closely packed (as in a column matrix) or loosely-packed particles.

Attachment of target molecules to a solid support may be achieved by tagging the target molecule with a tag molecule that binds to a capture element molecule immobilised on the solid support. By way of example, the tag molecule may be a biotin moiety and the capture element may be avidin or streptavidin. As such the solid support could be a streptavidin-coated bead or resin such as Dynabeads M-280 Streptavidin, Dynabeads MyOne Streptavidin, Dynabeads M-270 Streptavidin (Invitrogen), Streptavidin Agarose Resin (Pierce), Streptavidin Ultralink Resin, MagnaBind Streptavidin Beads (Thermo Scientific), BioMag Streptavidin, Pro Mag Streptavidin, Silica Streptavidin (Bangs Laboratories), Streptavidin Sepharose High Performance (GE Healthcare), Streptavidin Polystyrene Microspheres (Microspheres Nanospheres), Streptavidin Coated Polystyrene Particles (Spherotech), or any other streptavidin coated bead or resin commonly used by one skilled in the art to capture biotin-tagged molecules. Other suitable tag and capture element pairs include polyhistidine tags and anti-polyhistidine tag antibodies, and FLAG-tag (DYKXXD) and anti-FLAG antibody.

Optionally, the method may further comprise the step of dissociating the oligonucleotide construct:target molecule complex and/or isolating the oligonucleotide construct from the oligonucleotide construct:target molecule complex and/or identifying an oligonucleotide construct.

The method may further comprise the step of determining the sequence structure (base sequence and modification sequence) of the functional sequence, and optionally of any other sequence element of the oligonucleotide construct.

To determine the sequence structure of the functional sequence the sequence of the coding sequence may be determined, e.g. by amplification of the coding sequence using the fixed coding sequences to design primers for enzyme (e.g. polymerase) based amplification. Examples of amplification techniques are well-known to those of ordinary skill in the art and include PCR (Polymerase Chain Reaction), LCR (Ligase Chain Reaction), 3SR (Self-sustained Sequence Replication), SDA (Strand Displacement Amplification), RT-PCR, ICAN, and LAMP (e.g. see DNA Amplification Techniques: An Overview. David H. Sorscher., Molecular Diagnostics. Pathology and Laboratory Medicine. 1997, pp89-101).

Using a polymerase based amplification technique to read the coding sequence of the selected oligonucleotide construct a range of DNA and RNA modifications can be used in the coding sequence provided a nucleic acid polymerase can read the sequence. A wide range of suitable polymerases are known to those of ordinary skill in the art (e.g. see Eckert and Kunkel., PCR Methods Appl 1991 August; 1(1):17-24). One such polymerase is KOD DNA Polymerase (KOD HiFi DNA Polymerase) which is a recombinant form of *Thermococcus kodakaraensis* KOD1 DNA polymerase (Nishioka, M., et al. 2001. J. Biotechnol. 88, 141. Takagi, M., et al. 1997. Appl. Environ. Microbiol. 63, 4504).

Determining the base sequence of the amplified coding sequence can also be performed by one of several techniques well known to one of ordinary skill in the art, e.g. chain termination method, Sanger method, using a DNA sequencer (automated DNA base sequence determination), or by using a dideoxy method.

The sequence of the coding sequence may then be read in units of n, preferably in 5' to 3' direction, and translated, e.g. using the corresponding coding table, to indicate the sequence structure, preferably also in 5' to 3' direction, of the functional sequence.

Once the sequence structure of the functional sequence has been determined an oligonucleotide molecule may be prepared, e.g. synthesised, based on, and preferably comprising or consisting of, the sequence structure of the functional sequence, optionally including additional sequence elements at either the 3' or 5' end, or both. The re-synthesised oligonucleotide molecule may be assayed to check for retention of the property for which it was selected, e.g. binding affinity to a target molecule.

In general, the ability of a functional sequence containing oligonucleotide to modulate the functional activity of a target molecule can be assessed using in vitro and in vivo models, depending on the biological function of the target. In some embodiments, the functional sequence may inhibit or stimulate a known biological function of the target.

Accordingly, a method for producing an oligonucleotide molecule is provided, said method comprising the step of synthesising an oligonucleotide molecule based on the sequence structure of a functional sequence of an oligonucleotide construct identified by, or identifiable by, a method comprising contacting a mixture of different oligonucleotide constructs with a target molecule under conditions that permit the oligonucleotide construct and target molecule to bind and form an oligonucleotide construct: target molecule complex, and partitioning the complexes from unbound oligonucleotides and/or unbound target molecule, and optionally identifying an oligonucleotide construct capable of binding to the target molecule, and optionally determining the sequence structure of the functional sequence.

For example, such synthesis may be based on information, e.g. recorded on paper, in electronic form or available on the internet, recording the sequence structure of a functional sequence.

Following identification of an oligonucleotide construct or determination of a functional sequence it is possible to produce a composition, e.g. pharmaceutically useful composition or diagnostic composition, based on the construct or sequence so identified. In addition to the steps of the methods described herein, such methods of production may further comprise one or both of the following steps:

(a) identifying and/or characterising the structure of a selected oligonucleotide construct, functional element or functional sequence;

(b) preparing, e.g. synthesising, an oligonucleotide based on, comprising or consisting of, the sequence structure of the selected oligonucleotide construct, functional element or functional sequence;

and optionally one of the following steps:

(c) mixing the prepared oligonucleotide with a carrier, adjuvant or diluent, or (d) attaching or adhering the prepared oligonucleotide to a diagnostic product, e.g. an array, chip, sensor, probe, lateral flow device, microfluidic device or test strip, optionally at one or more predetermined addresses or locations.

For example, a further aspect of the present invention relates to a method of formulating, preparing or producing a pharmaceutical or diagnostic composition, the method comprising preparing or synthesising an oligonucleotide based on, and preferably comprising or consisting of, the sequence structure of the selected oligonucleotide construct, functional element or functional sequence, and further comprising the step of (i) formulating a pharmaceutical composition by mixing the oligonucleotide with a pharmaceutically acceptable carrier, adjuvant or diluent or (ii) formulating a diagnostic composition by attaching or adhering the prepared oligonucleotide to a diagnostic product, e.g. an array, chip, sensor, probe, lateral flow device, microfluidic device or test strip, optionally at one or more predetermined addresses or locations.

Suitable selection techniques may include affinity chromatography, filter binding assay, liquid-liquid partition, filtration, gel shift, density gradient centrifugation, e.g. as described in U.S. Pat. No. 7,517,646 B2, specifically incorporated herein by reference. Affinity chromatography is a well-known separation and purification method in which the target may be immobilized on a column which is equilibrated with a buffer solution. A solution containing a pool or library of oligonucleotide constructs is poured into the column. Oligonucleotide sequences having affinity for the target adsorb to the column. Washing with the buffer solution allows removal of unbound agents. Oligonucleotides that bind to the column may be released and collected, e.g. by passing a solution containing the target molecule or a diluted buffer solution through the column.

By way of example of how an oligonucleotide construct library may be screened to identify an oligonucleotide construct having a particular property, in some embodiments a combinatorial library of particle/bead/microcarrier-bound oligonucleotide constructs may be assayed for binding affinity using an immunofluorescence assay. The library may be contacted with purified target molecule immobilised on a solid support. The support may be washed to partition oligonucleotide construct:target molecule complexes from unbound oligonucleotide constructs. The complexes may then be contacted with an anti-target molecule antibody (primary antibody) and then contacted with a fluorescently labelled anti-primary antibody. Beads may then be visualised for fluorescence, selected and subject to PCR amplification of the coding sequence. In some embodiments, selection of beads may be made by flow cytometry in which fluorescently labelled beads are detected and separated from unlabelled beads or beads labelled with a different fluorescent label (e.g. see Yang X, et al. Immunofluorescence assay and flow cytometry selection of bead-bound aptamers. *Nucleic Acids Research* 31(10) (2003) e54). Such techniques allow for high throughput screening and identification of oligonucleotide constructs that bind to the target molecule.

Functional Sequence Oligonucleotides

In some aspects of the present invention an oligonucleotide construct is provided that enables generation and screening of a large number of different functional sequences, each containing at least one nucleotide, preferably at least two or at least three adjacent nucleotides, having a functional substituent. In some preferred embodiments the functional substituent is an amino acid side chain.

Following identification of an oligonucleotide construct, the sequence structure of the functional sequence may be determined and recorded as information defining the functional sequence. A new oligonucleotide molecule may be prepared based on the recorded information which oligonucleotide molecule comprises all or a part of the functional sequence (including functional substituents).

The new oligonucleotide may comprise, or consist, of the sequence structure of the functional sequence, optionally together with the fixed sequences. More commonly, it will comprise the sequence structure of the functional sequence, or a substantial part of it, and may further comprise one or more additional nucleotide sequence elements and/or be derivatised by conjugation to one or more other molecules which may or may not be oligonucleotides or nucleic acids.

The functional sequence may have a minimum length selected from one of 3, 4, 5, 6, 7, 8, 9, 10, 11, 12, 13, 14, or 15 nucleotides and a maximum length selected from one of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. In preferred embodiments the functional sequence may have a length of one of 10, 11, 12, 13, 14, 15, 16, 17, 18, 19, 20, 21, 22, 23, 24, 25, 26, 27, 28, 29, or 30 nucleotides. In particularly preferred embodiments the functional sequence has a length of one of 10, 11, 12, 13, 14 or 15 nucleotides. In one preferred embodiment the functional sequence has 13 nucleotides.

Preferably at least two, or at least three or four, adjacent nucleotides in a contiguous sequence element of the functional sequence are modified by incorporation of a functional substituent, as described herein. In some embodiments one of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 adjacent nucleotides in a contiguous sequence element of the functional sequence are modified by incorporation of such a substituent. In some embodiments each nucleotide in the functional sequence is modified by incorporation of such a substituent. In other embodiments, one or more nucleotides in the functional sequence are not modified by incorporation of such a substituent.

In some preferred embodiments the functional sequence consists of a contiguous sequence of one of 10, 11, 12, 13, 14 or 15 nucleotides in which each or all except for one of 1, 2, 3, 4 or 5 nucleotides are modified by incorporation of a functional substituent, as described herein.

A substantial part of the functional sequence may be a sequence having at least 70% identity to the sequence structure of the functional sequence. For the functional sequence, sequence structure identity may be calculated by aligning sequence elements but also requires the presence/absence of functional substituents (for example, amino acid moiety substituents) to be considered in determining identity. Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

In addition the new oligonucleotide molecule may comprise a sequence element at one or both of the 3' and 5' ends, e.g. sequence elements having known sequence and may be designed as primers for polymerase amplification and/or as sequences that will hybridise to form a stem-loop structure (e.g. complementary sequences) or will otherwise provide structural stability to the functional sequence. These sequences preferably do not contain functional substituents, as described herein, although may include other chemical modifications, such as chemical substitution at a sugar position, a phosphate position, and optionally a base position of the nucleic acid including, for example, incorporation of a modified nucleotide, incorporation of a capping moiety (e.g. 3' capping, 5' capping, inverted dT 3'-3' capping), substitutions or modifications in the phosphate backbone, e.g. monothioate, dithioate, methyl phosphonate, alkyl phosphonate. Sugar modifications may include (deoxy)-ribose, 2'-amine nucleotides (2'-NH$_2$), 2'-fluoro nucleotides (2'-F), and 2'-O-methyl (2'-OMe) nucleotides.

The new oligonucleotide molecule may also be conjugated to other molecules. For example, conjugation may be to molecules that improve resistance to degradation or clearance from the body, such as to high molecular weight, optionally non-immunogenic, molecules, e.g. polyethylene glycol.

Derivatization of nucleic acids with high molecular weight non-immunogenic polymers has the potential to alter the pharmacokinetic and pharmacodynamic properties of nucleic acids making them more effective and/or safer therapeutic agents. Changes in activity can include increased resistance to degradation by nucleases, reduced clearance from the body, decreased exposure to the immune system, and altered distribution of the therapeutic through the body.

The oligonucleotides according to the present the invention, in particular oligonucleotide molecules comprising a functional sequence, may be derivatized with one or more polyalkylene glycol ("PAG") moieties, e.g. polyethylene glycol ("PEG"), and polypropylene glycol (including poly isopropylene glycol). Random or block copolymers of different alkylene oxides can also be used in many applications. PAG derivatized compounds conjugated to the oligonucleotides of the invention are typically between 5 and 80 kDa in size.

Methods for generating high molecular weight PEG-oligonucleotide conjugates involve the formation of a linear activated PEG, or a branched activated PEG in which two or more PEGs are attached to a central core carrying the activated group. The terminal portions of these high molecular weight PEG molecules, i.e. the relatively non-reactive hydroxyl (—OH) moieties, can be activated or converted to functional moieties for attachment of one or more of the PEGs to other compounds at reactive sites on the compound. Branched activated PEGs will have more than two termini, and in cases where two or more termini have been activated it may be desirable to cap the PEG molecule on one end with an essentially non-reactive moiety so that the PEG molecule is mono-functional (or mono-activated). The other, un-capped terminus of the PEG molecule typically is converted to a reactive end moiety that can be activated for attachment at a reactive site on the oligonucleotide.

Conjugation may also be to labelling agents which may help visualisation of the oligonucleotide which may be relevant to research and diagnostic applications. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. $^{32}$P, $^{33}$P, $^{35}$S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Additional labelling materials include biotin, a ligand, a specific nucleic acid, a protein, or a hapten.

Conjugation may also be to one or more active agents such as to a therapeutically active agent. Examples of therapeutically active agents include small molecule pharmaceuticals (such as antibiotics, DNA intercalators, protein kinase inhibitors) and biological agents (such as an antibody, antibody fragment, nucleic acid aptamer, peptide aptamer, nucleic acid (e.g. DNA, RNA), peptide, polypeptide, or protein).

In this context, it is noted that in some embodiments the oligonucleotide molecule may have independent activity as a therapeutic agent, i.e. have therapeutic effect and be an 'active agent' in the context of actual or potential therapeutic treatment. For example it may act as an agonist or antagonist of a target molecule and thereby provide or initiate a treatment effect. In other embodiments the oligonucleotide molecule may not have a therapeutic effect, i.e. may not be an 'active agent', but may act to target a conjugated active agent to the target molecule, or cells/tissues expressing the target molecule.

The functional sequence may optionally be truncated in order to identify a minimal sequence having the desired property, e.g. target molecule binding and/or functional characteristic. Truncation experiments may be guided by the use of folding programs and sequence analysis, e.g. analyzing functional sequences to identify conserved motifs of amino acid substituents and/or nucleotide backbone and/or using covariation to guide the design of truncated sequences. Folding programs include, the RNA structure program (Mathews, D. H.; Disney, M. D.; Childs, J. L.; Schroeder, S. J.; Zuker, M.; and Turner, D. H., "Incorporating chemical modification constraints into a dynamic programming algorithm for prediction of RNA secondary structure," 2004. Proceedings of the National Academy of Sciences, US, 101, 7287-7292). Truncated sequences can be chemically synthesized and tested for binding and functional characteristics, as compared to the non-truncated sequence from which they were derived. Variants of the functional sequence containing 5', 3' and/or internal deletions may also be chemically synthesized and tested for binding and/or functional characteristics, as compared to the non-modified sequence from which they were derived.

The new oligonucleotide molecule may also be designed to include chemical modifications not present in the functional sequence of the oligonucleotide construct from which it was derived. Such modifications preferably do not alter the structure or order of functional substituents (as defined herein) present in the functional sequence, and optionally do not alter the chemical structure of the corresponding base(s), and may be included in order to improve the resistance to degradation, e.g. nuclease degradation, of the molecule. Suitable modifications may be selected from the group consisting of: a chemical modification at a sugar position; a chemical modification at a base position and a chemical modification at an internucleotide linkage. Suitable examples include inclusion of phosphorothioate, phosphodiester or phosphorodithioate linkages, inclusion of 2'-deoxy, 2'-OH nucleotide, 2'-OMe, 2'-fluoro or 2'-NH$_2$ sugar modifications; and the addition of one or more PEG or other polymers.

Oligonucleotide molecules comprising the functional sequence and selected for binding to a target molecule have an affinity and specificity comparable to those of an antibody and can be used in a corresponding range of applications.

Complexes

Oligonucleotide molecules according to the present invention, in particular oligonucleotides comprising a functional sequence, may be provided as a complex with a target molecule. Preferably the complex is the product of a high affinity binding interaction between the functional sequence and target molecule. Although the complex may comprise an oligonucleotide covalently bonded to the target molecule, preferably it is a non-covalent complex. Non-covalent complexes may be maintained by hydrogen bonding, van der Waal forces and optionally ionic interaction.

Complexes may be provided in isolated form, or in purified form, or may be present in a solution or mixture with other molecules. Complexes may be provided ex vivo or in vitro or may be formed in vivo.

For example, complexes may be formed during selection for oligonucleotides that bind to a target molecule and may be present before and after partitioning from other molecules. Complexes may also be formed when carrying out assays designed to detect the presence of a target molecule.

In some embodiments, complexes may be formed and/or isolated on a solid support or support matrix, and may be bound, optionally releasably bound, to the support. Immobilisation of the complex on a support may be achieved by binding the oligonucleotide or target molecule to the support, e.g. using a biotin:avidin binding pair in which one component of the pair is bound to the support and the other to the oligonucleotide or target molecule.

Detection of Target Molecule

Oligonucleotide molecules according to the present invention that bind a target molecule, in particular oligonucleotides comprising a functional sequence, may be utilised in a method of detecting the presence of a target molecule. Such methods may preferably be performed in vitro or ex vivo, or optionally in vivo.

As such, a method may be provided, the method comprising contacting an oligonucleotide molecule according to the present invention with a sample containing, or suspected of containing, a target molecule which the oligonucleotide is capable of binding, e.g. with high affinity, and detecting the formation of an oligonucleotide:target molecule complex.

In one aspect of the present invention a method of detecting a target molecule is provided, the method comprising contacting an oligonucleotide molecule according to the present invention which is capable of binding a target molecule with a sample containing, or suspected of containing, said target molecule; allowing oligonucleotide:target molecule complex(es) to form; detecting said oligonucleotide:target molecule complex(es).

In some embodiments the oligonucleotide may be immobilised on a solid support or support matrix, e.g. on a slide, strip, chip, array column etc.

The sample may be of any kind. For example, it may comprise a mixture of molecules including, or suspected of including, the target molecule. In some embodiments the sample may be a biological sample. In other embodiments the sample may be an environmental sample, e.g. sample of water, earth or air. The sample may be treated before being contacted with the oligonucleotide, e.g. mixed with a solvent or carrier or processed to remove, or retain, a fluid or solid component.

Biological samples may comprise or may be derived from: a quantity of blood; a quantity of serum derived from an individual's blood which may comprise the fluid portion of the blood obtained after removal of the fibrin clot and blood cells; a quantity of pancreatic juice; a tissue sample or biopsy; or cells isolated from said individual. A biological sample may be taken from any tissue or bodily fluid, e.g. a blood sample, blood-derived sample, serum sample, lymph sample, semen sample, synovial fluid sample, saliva sample. A blood derived sample may be a selected fraction of a patient's blood, e.g. a selected cell-containing fraction or a plasma or serum fraction.

Assays may be of known formats, e.g. sandwich assays, and immunoassays, in which the oligonucleotide forms one of the binding agents.

Compositions

Compositions or preparations may be provided comprising one or more oligonucleotide constructs or oligonucleotides according to the present invention. In some embodiments compositions or preparations may be prepared to be suitable for use in research, therapy or diagnostic applications.

Typically, a composition will comprise one or more isolated or purified oligonucleotide constructs or oligonucleotide molecules, optionally an oligonucleotide construct or oligonucleotide molecule synthesised de novo, together with a suitable carrier, excipient, diluent, solvent, support matrix, or solid support.

It may be convenient or desirable to prepare, purify, and/or handle a corresponding salt of the oligonucleotide construct or oligonucleotide, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Unless otherwise specified, a reference to an oligonucleotide construct or oligonucleotide also includes salt forms thereof.

It may be convenient or desirable to prepare, purify, and/or handle a corresponding solvate of the oligonucleotide construct or oligonucleotide. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

Unless otherwise specified, a reference to an oligonucleotide construct or oligonucleotide also includes solvate forms thereof.

Compositions, preparation and formulations may be packaged for use in a variety of pharmaceutically acceptable containers using any pharmaceutically acceptable container closure, as the formulations are compatible with PVC-containing and PVC-free containers and container closures. Examples of pharmaceutically acceptable containers include, but are not limited to, ampuls, pre-filled syringes, intravenous bags, intravenous bottles and admix bags.

Preferably, the formulations, compositions and preparations are sterile. A "sterile" formulation is a formulation that has been brought to a state of sterility and has not been subsequently exposed to microbiological contamination, i.e. the container holding the sterile composition has not been compromised. Sterile compositions are generally prepared by pharmaceutical manufacturers in accordance with current Good Manufacturing Practice ("cGMP") regulations.

Compositions, preparations and formulations may also be packaged in a kit. The kit will contain the composition, formulation or preparation along with instructions for its use, e.g. in diagnosis, research or therapy. The kit may also contain one or more of the following: a syringe, an intravenous bag or bottle, the same drug in a different dosage form or another drug. A suitable kit may have at least one container having a predetermined quantity or concentration of oligonucleotide according to the present invention. The oligonucleotide may be formulated so as to be suitable for administration to a subject. In some embodiments the oligonucleotide may be provided in the form of a diagnostic composition, as described herein.

In some embodiments a kit comprises an oligonucleotide construct and a coding table describing the relationship between n-mers of the coding sequence and nucleotides at a corresponding position in the functional sequence. Where a plurality of oligonucleotide constructs are provided a plurality of respective coding tables may also be provided in the kit. Similarly, a library of oligonucleotide constructs may be provided, e.g. in the form of a library of beads, and a plurality of respective coding tables may also be provided with the library.

In some embodiments, the composition is a pharmaceutical composition (e.g. formulation, preparation, medicament) comprising an oligonucleotide construct or oligonucleotide, as described herein, and a pharmaceutically acceptable carrier.

In one embodiment, the composition is a pharmaceutical composition comprising at least one oligonucleotide construct or oligonucleotide, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition may further comprise other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, New York, USA), Remington's Pharmaceutical Sciences, 20th edition, pub. Lippincott, Williams & Wilkins, 2000; and Handbook of Pharmaceutical Excipients, 2nd edition, 1994.

Another aspect of the present invention pertains to methods of making a pharmaceutical composition comprising admixing at least one oligonucleotide construct or oligonucleotide together with one or more other pharmaceutically acceptable ingredients well known to those skilled in the art, e.g. carriers, diluents, excipients, etc. If formulated as discrete units (e.g. tablets, etc.), each unit contains a predetermined amount (dosage) of the active compound.

The term "pharmaceutically acceptable" as used herein pertains to compounds, ingredients, materials, compositions, dosage forms, etc. which are, within the scope of sound medical judgment, suitable for use in contact with the tissues of the subject in question (e.g. human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the oligonucleotide construct or oligonucleotide with a carrier which constitutes one or more accessory ingredients. In general, the formulations are prepared by uniformly and intimately bringing into association the active compound with carriers (e.g. liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g. aqueous, non-aqueous), suspensions (e.g. aqueous, non-aqueous), emulsions (e.g. oil-in-water, water-in-oil), elixirs, syrups, electuaries, mouthwashes, drops, tablets, gels, pastes, ointments, creams, lotions, oils, foams, sprays, mists, or aerosols.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Solvents may conveniently be classified according to one or more of their physical or chemical properties.

For example, solvents may be classified according to their polarity, that is, their permanent dipole moment. Examples of highly polar solvents include dimethylformamide (DMF), dimethylacetamide, and acetonitrile (ACN). Examples of moderately polar solvents include acetone, methanol, tetrahydrofuran (THF), ethyl acetate (AcOEt), and water. Examples of relatively non-polar solvents include diethyl ether, chloroform, and dichloromethane (DCM). Examples of non-polar and virtually non-polar solvents include alkanes, benzene, toluene, and carbon tetrachloride.

Solvents may also be classified as "protic" or "aprotic" according to their proton-exchange properties. Protic solvents accept and/or donate protons. Examples of protic solvents include water, alcohols, carboxylic acids (e.g. acetic acid), and amines (e.g. ammonia, pyridine). Aprotic solvents neither accept nor donate protons. Examples of aprotic solvents include carbon tetrachloride, chloroform, dichloromethane (DCM), acetonitrile (ACN), ethyl acetate (AcOEt), dimethylacetamide, tetrahydrofuran (THF), dimethylformamide (DMF), toluene, benzene, acetone, ethers (e.g. diethyl ether), alkanes (e.g. hexane), dimethylsulfoxide (DMSO), sulfur dioxide, hexamethylphosphoramide (HMPA), and, tetramethylurea. Amphoteric solvents, such as water, are capable of both accepting and donating protons.

Solvents may also be classified as "organic" or "inorganic" according to their chemical composition. Conventionally, organic solvents comprise, at least, carbon atoms, while inorganic solvents do not. Examples of inorganic solvents include water, ammonia, and sulfur dioxide.

In some aspects of the present invention, an oligonucleotide construct or oligonucleotide molecule according to the present invention is provided for use in therapy.

In one aspect of the present invention a method of treating a disease or condition is provided, the method comprising administering an oligonucleotide construct or oligonucleotide molecule according to the present invention to a subject requiring treatment.

In another aspect of the present invention an oligonucleotide construct or oligonucleotide molecule according to the present invention is provided for use in a method of medical treatment.

In another aspect of the present invention an oligonucleotide construct or oligonucleotide molecule according to the present invention is provided for use in a method for treatment of the human or animal body by surgery or therapy or in a diagnostic method practised on the human or animal body.

In another aspect of the present invention an oligonucleotide construct or oligonucleotide molecule according to the present invention for use in the treatment of a disease or condition is provided.

In another aspect of the present invention use of an oligonucleotide construct or oligonucleotide molecule according to the present invention in the manufacture of a pharmaceutical composition or medicament is provided for use in the treatment of a disease of condition.

The oligonucleotide construct or oligonucleotide molecule may be formulated as a pharmaceutical composition, as described above. The therapeutic effect may be provided by binding of the oligonucleotide construct or oligonucleotide molecule to a target molecule in the body of a subject requiring treatment. As such, the oligonucleotide construct or oligonucleotide may be one that binds to a target molecule associated with, or that mediates, the disease or condition to be treated.

The subject to be treated may be any animal or human. The subject is preferably mammalian, more preferably human. The subject may be a non-human mammal, but is more preferably human. The subject may be male or female. The subject may be a patient.

Medicaments and pharmaceutical compositions according to aspects of the present invention may be formulated for administration by a number of routes, including but not limited to, parenteral, intravenous, intra-arterial, intramuscular, oral and nasal. The medicaments and compositions may be formulated in fluid, solid or other form. Fluid formulations may be formulated for administration by injection to a selected region of the human or animal body.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Oligonucleotide constructs or oligonucleotide molecules may be used to treat, prevent or ameliorate a disease or condition mediated by a target molecule, e.g. a target protein. In principle, the precise disease or condition to be treated, prevented or ameliorated may of any kind in which a target molecule, particularly a target protein, plays a role and may be modulated, e.g. inhibited or stimulated, to affect the progression of the disease or occurrence/continuance of some or all of its symptoms. By way of example, diseases may include cancer, heart disease, hypertension, HIV/AIDS, and diabetes.

In some embodiments the composition is suitable for use in detecting target molecules, and may be formulated as a research or diagnostic composition.

Such compositions may comprise one or a plurality of oligonucleotide constructs or oligonucleotides with a suitable carrier, excipient, diluent, solvent, support matrix, or solid support.

The oligonucleotide construct(s) or oligonucleotide(s) may be labelled with an agent that permits detection of the oligonucleotide construct or oligonucleotide, e.g. when bound to a target molecule. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. $^{32}P$, $^{33}P$, $^{35}S$), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Additional labelling materials include biotin, a ligand, a specific nucleic acid, a protein, or a hapten.

The oligonucleotide constructs or oligonucleotides of the invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any oligonucleotide by procedures known in the art to incorporate a labeling tag to track the presence of such an oligonucleotide. Such a tag could be used in a number of diagnostic procedures.

In some embodiments, the composition is a diagnostic composition, being suitable for use in a method of diagnosis of a disease or condition, which method may be performed in vitro, ex vivo, or optionally in vivo.

A method of diagnosis of a disease or condition may comprise contacting an oligonucleotide construct or oligonucleotide molecule according to the present invention with a sample containing a target molecule which the oligonucleotide is capable of binding, e.g. with high affinity, and detecting the formation of an oligonucleotide:target molecule complex. Formation of the complex may produce a detectable signal, e.g. a colour change.

Such methods may involve detecting the presence or absence of a target molecule from a sample, as described above. Optionally, the methods may further comprise the step of determining a diagnosis for a subject from which the sample was taken.

In some embodiments a diagnostic product is provided, e.g. in the form of an array, chip, sensor, probe, lateral flow device, microfluidic device or test strip. The diagnostic product may have one or a plurality of oligonucleotide constructs or oligonucleotides immobilised on it at one or a plurality of predetermined locations or addresses. The oligonucleotide constructs or oligonucleotides may be of the same type and/or capable of detecting the same target molecule, or of different types and/or capable of detecting different target molecules. Where oligonucleotide constructs or oligonucleotides of different types or capable of detecting different target molecules are used a single address or location may have only oligonucleotide constructs or oligonucleotides of the same type and/or capable of detecting the same target molecule. Detection of a target molecule may trigger a signal, e.g. change in colour, indicating an outcome of a diagnostic test.

Methods according to the present invention may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

The invention includes the combination of the aspects and preferred features described except where such a combination is clearly impermissible or expressly avoided.

The section headings used herein are for organizational purposes only and are not to be construed as limiting the subject matter described.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

and fixed sequences (white) and is attached to the support matrix via a spacer sequence. The coding element contains the coding sequence (diagonal line shading), coding-table ID sequence, fixed sequences and is attached to the support matrix via a spacer sequence.

Figure 1:
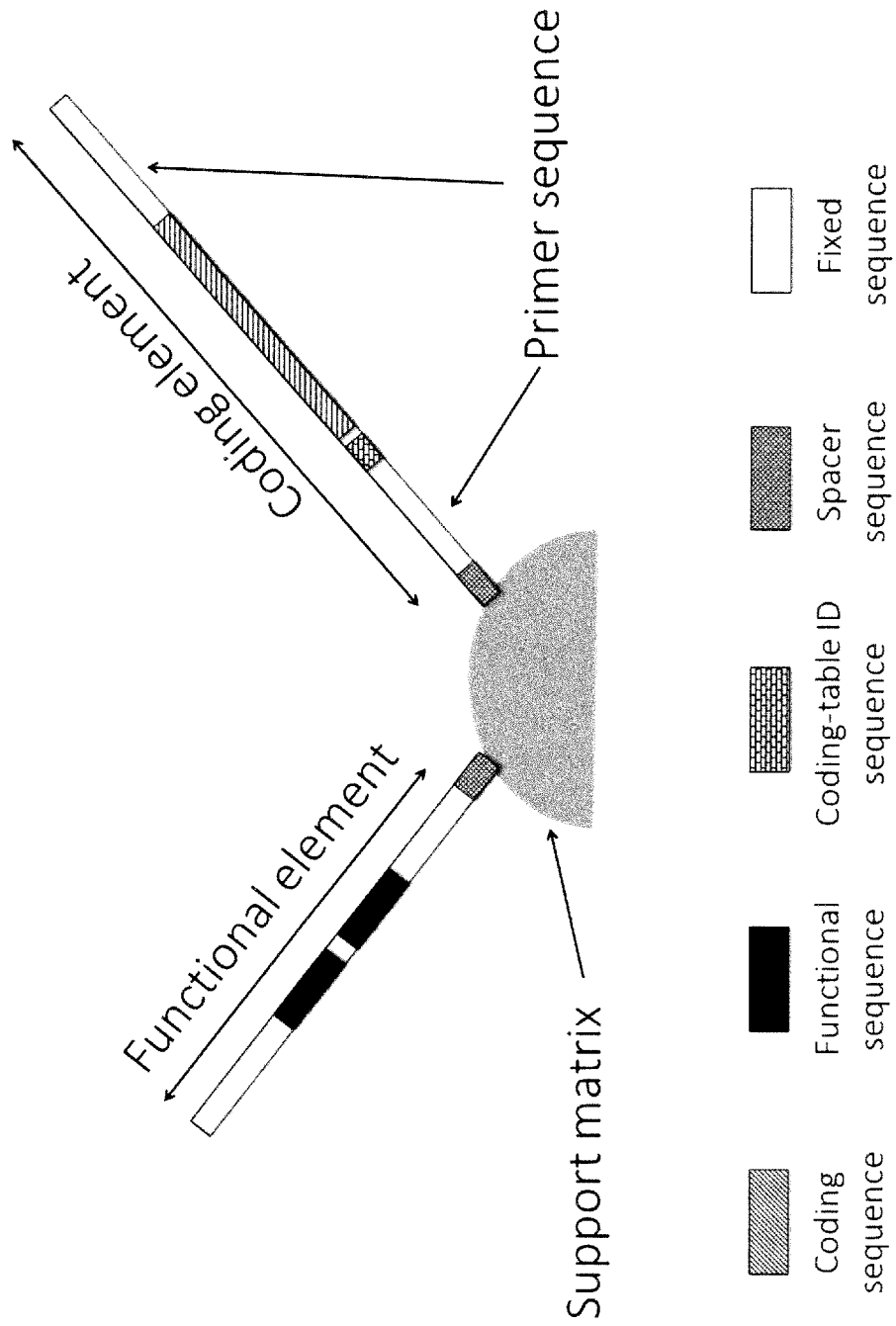
FIG. 1. Diagram of an oligonucleotide construct attached to a support matrix during synthesis of a library on support matrix (herein referred to as a "Library on Support"). Functional element contains the functional sequence (black)
Figure 2A:
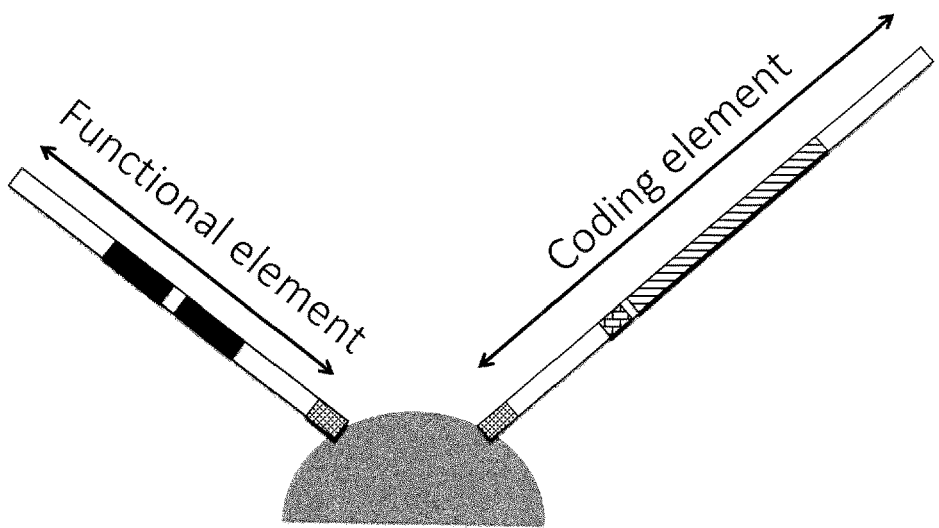
Figure 2B:
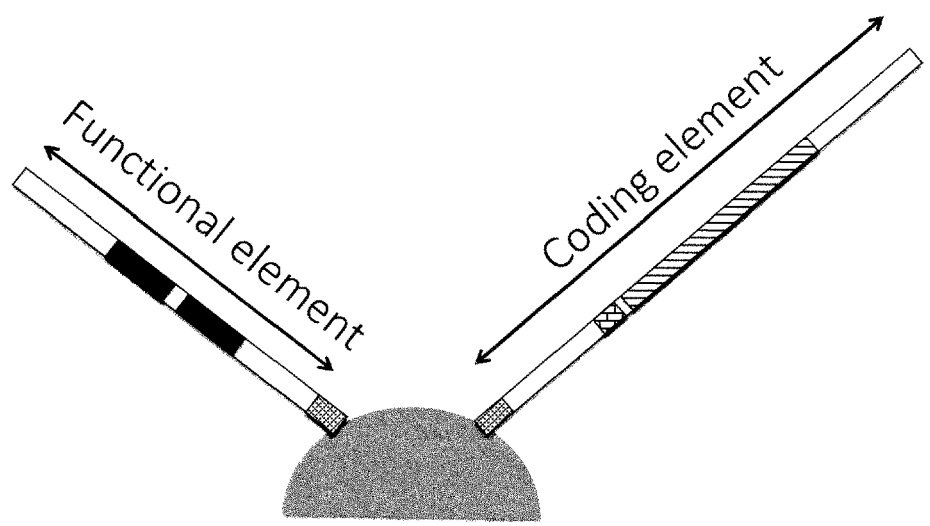
Figure 2C:
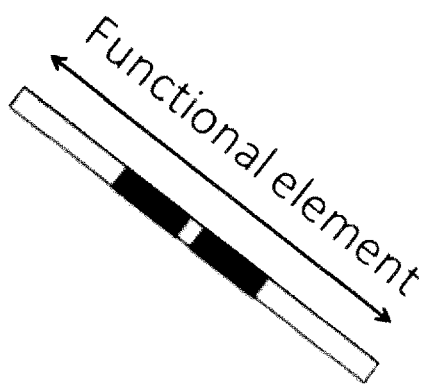

FIGS. 2A, 2B and 2C. (A) Diagram of an oligonucleotide construct (Library on Support) attached to a support matrix during synthesis of the oligonucleotide construct. (B) Diagram of an oligonucleotide construct (Library on Support) attached to a support matrix during selection of effective oligonucleotide construct. (C) Diagram of a selected functional element.

Figure 3:
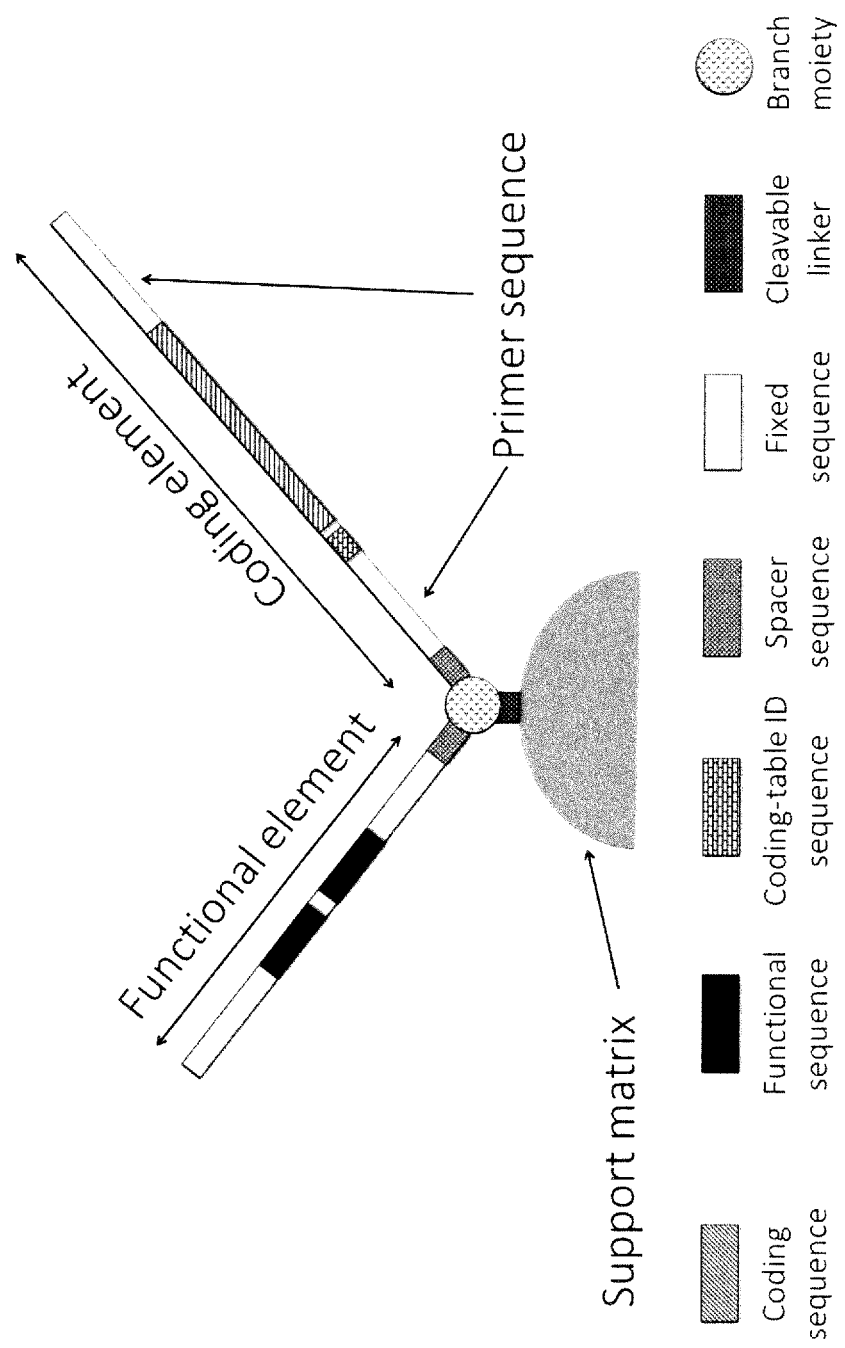

FIG. 3. Diagram of an oligonucleotide construct attached to a support matrix during synthesis of a Library in Solution. Functional element contains functional sequence (black), fixed sequences (white) and is attached to a branch moiety via a spacer sequence. The coding element contains the coding sequence (diagonal line shading), coding-table ID sequence, and fixed sequences and is attached to the branch moiety via a spacer sequence. The oligonucleotide construct is attached to the support matrix via a cleavable linker attached to the branch moiety.

Figure 4A:
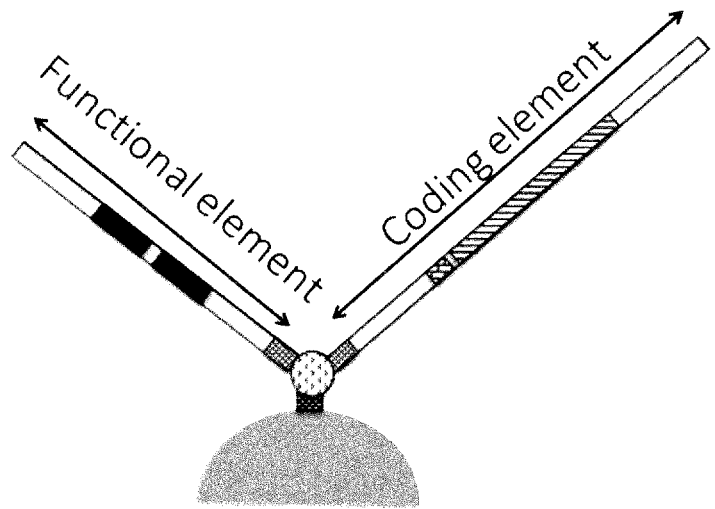
Figure 4B:
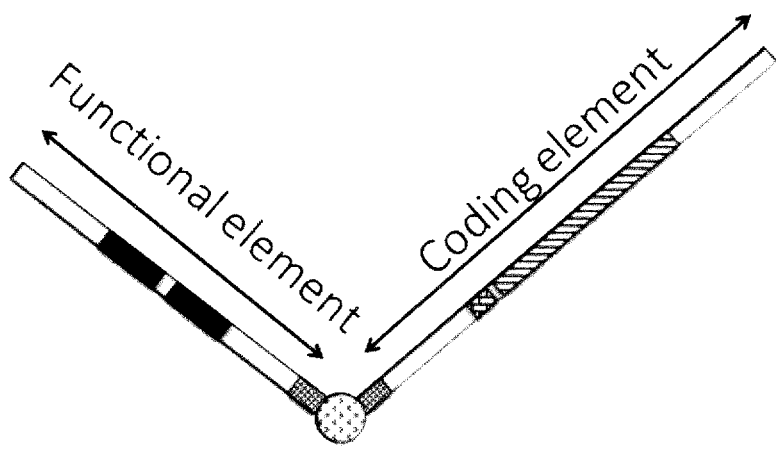
Figure 4C:
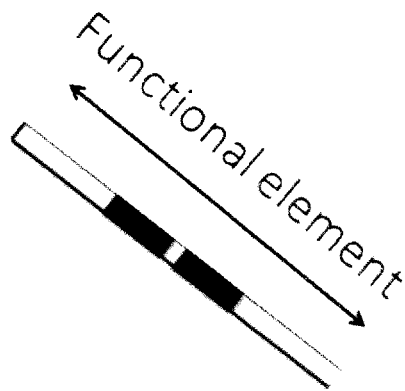

FIGS. 4A, 4B and 4C. (A) Diagram of an oligonucleotide construct (Library in Solution) attached to a support matrix during synthesis of the oligonucleotide construct. (B) Diagram of an oligonucleotide construct (Library in Solution) released from the support matrix during selection of effective oligonucleotide construct. (C) Diagram of a selected functional element.

Figure 5:
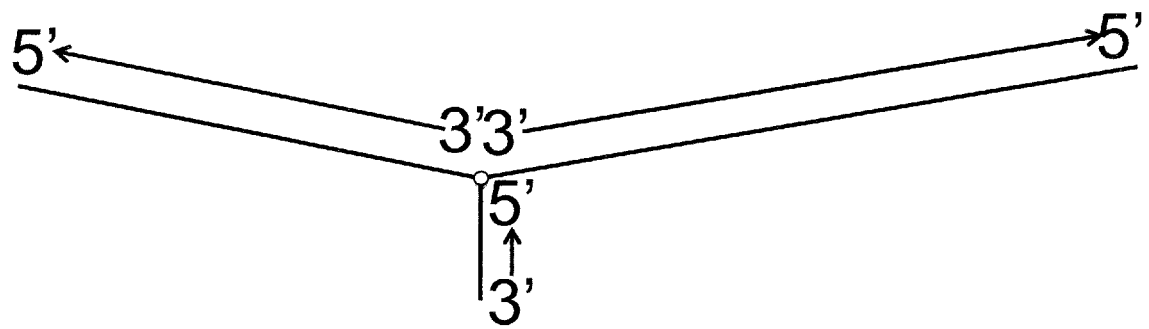

FIG. 5. Diagram showing orientation of functional element, coding element and linker sequence for oligonucleotide construct according to Library in Solution. The functional and coding elements are each synthesised in 3' to 5' direction away from the branch moiety. Linker sequence is in 3' to 5' direction towards the branch moiety.

Figure 6A:
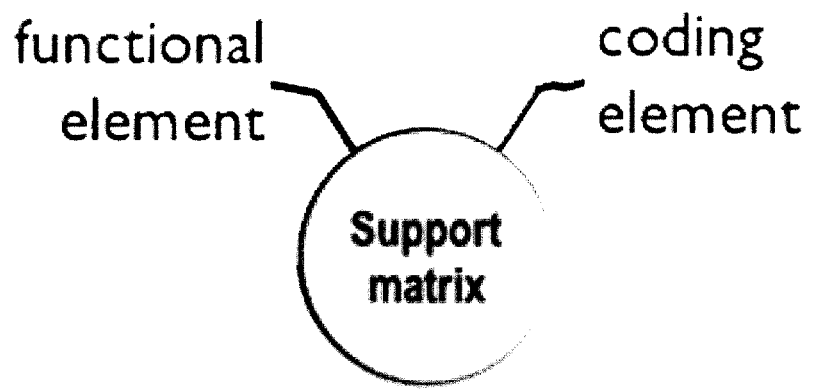
Figure 6B:
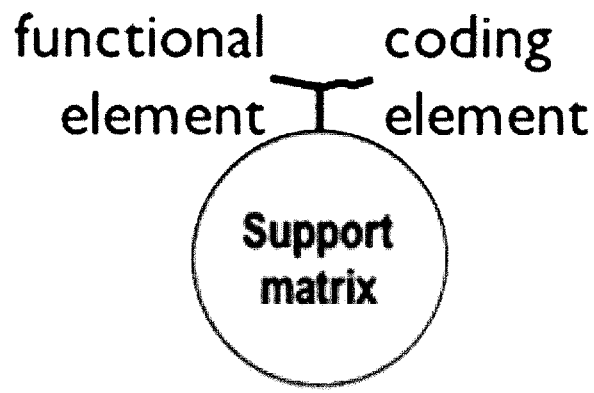
Figure 7A:
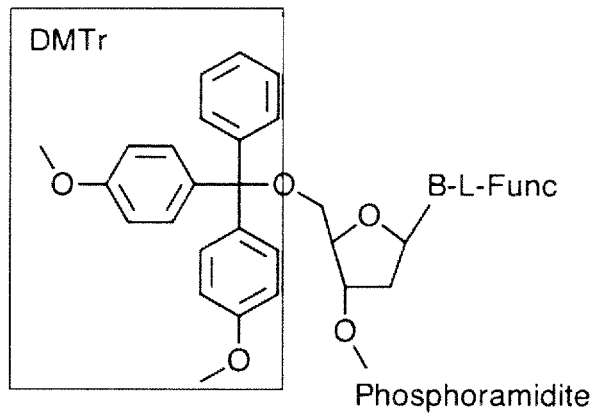
Figure 7B:
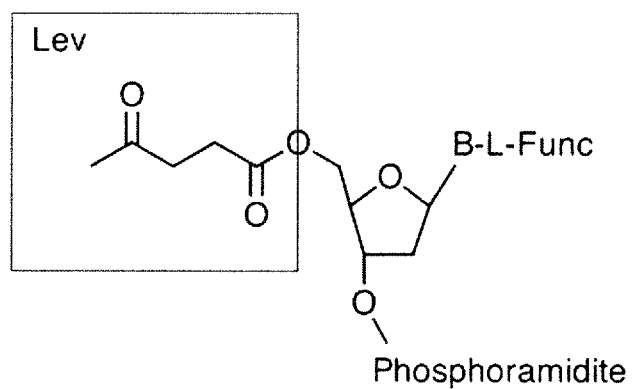
Figure 7C:
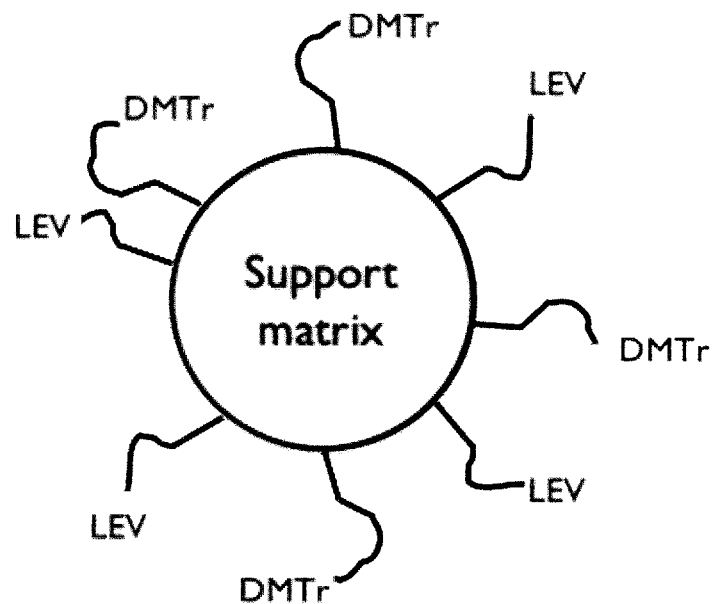
Figure 7D:
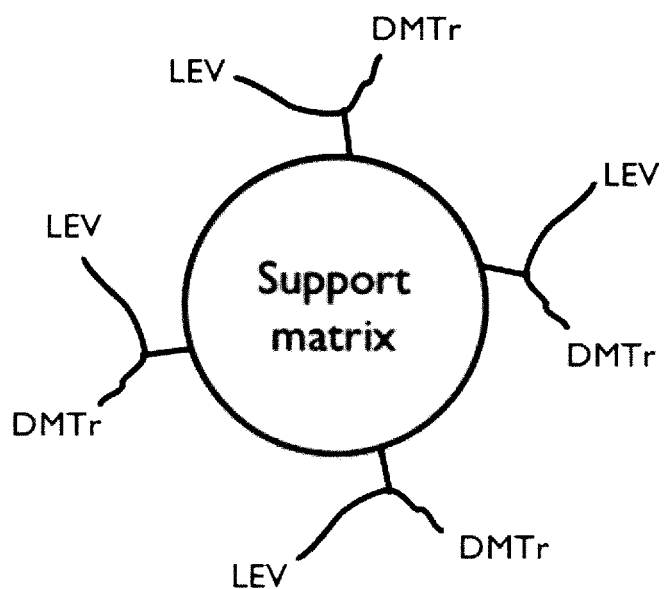

FIGS. 6A and 6B. (A) Illustration of an oligonucleotide construct having separate functional and coding elements attached to a support matrix. (B) Illustration of an oligonucleotide construct comprising a branched oligonucleotide attached to a support matrix, the branched oligonucleotide comprising a functional and coding elements.

FIGS. 7A, 7B, 7C and 7D. (A) 4,4'-dimethoxytrityl (DMTr) protected phosphoramidite. (B) Levulinoyl (Lev) protected phosphoramidite. (C) Illustration of a bead having a plurality of functional elements attached each protected with a 4,4'-dimethoxytrityl group and also having a plurality of coding elements attached each protected with a levulinoyl acid group. (D) Illustration of a bead having a plurality of branched oligonucleotide construct having a functional element protected with a 4,4'-dimethoxytrityl group and coding element protected with a levulinoyl group.

Figure 8:
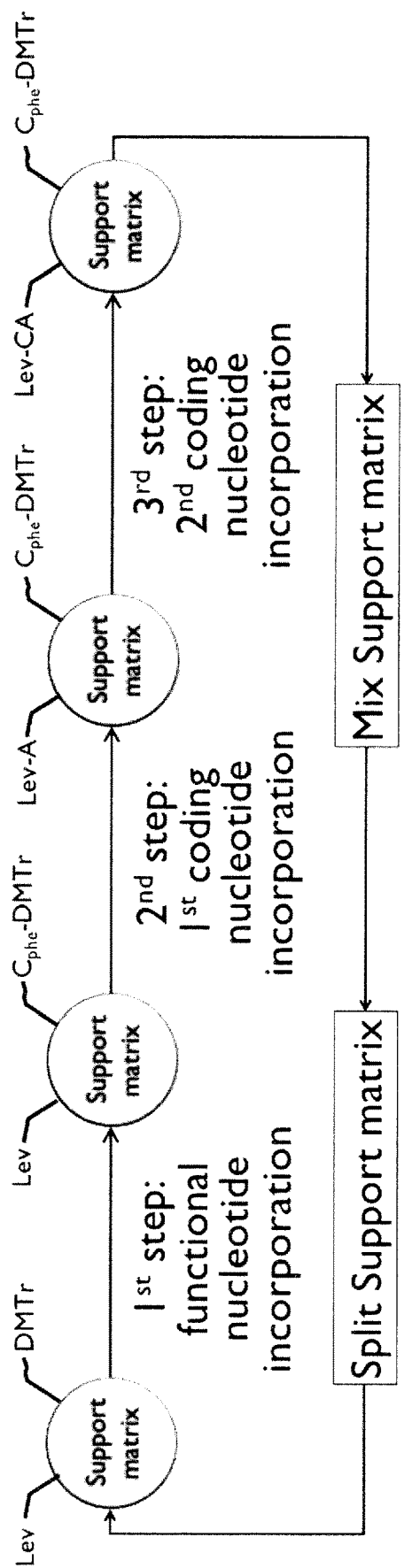

FIG. 8. Illustration of stepwise extension of functional and coding sequences and preparation of a combinatorial library. Extension of functional sequence with a modified nucleotide monomer is followed by extension of the coding sequence by addition of a non-modified nucleotide n-mer to form an oligonucleotide construct. Two protection groups (4,4'-dimethoxytrityl (DMTr) and Levulinoyl (Lev)) groups are used for synthesis of the oligonucleotide construct on a support matrix, one is used to protect the growing functional element and the other to protect the growing coding element. Serial de-protection and re-protection allows stepwise extension of the functional and coding elements. Mixing and re-splitting of support matrix of different constructs being simultaneously but separately prepared by the same process after one extension of each of the coding and functional sequences provides for formation of a combinatorial library of constructs having different functional sequences. The process illustrated can be repeated as many times as desired.

Figure 9A:
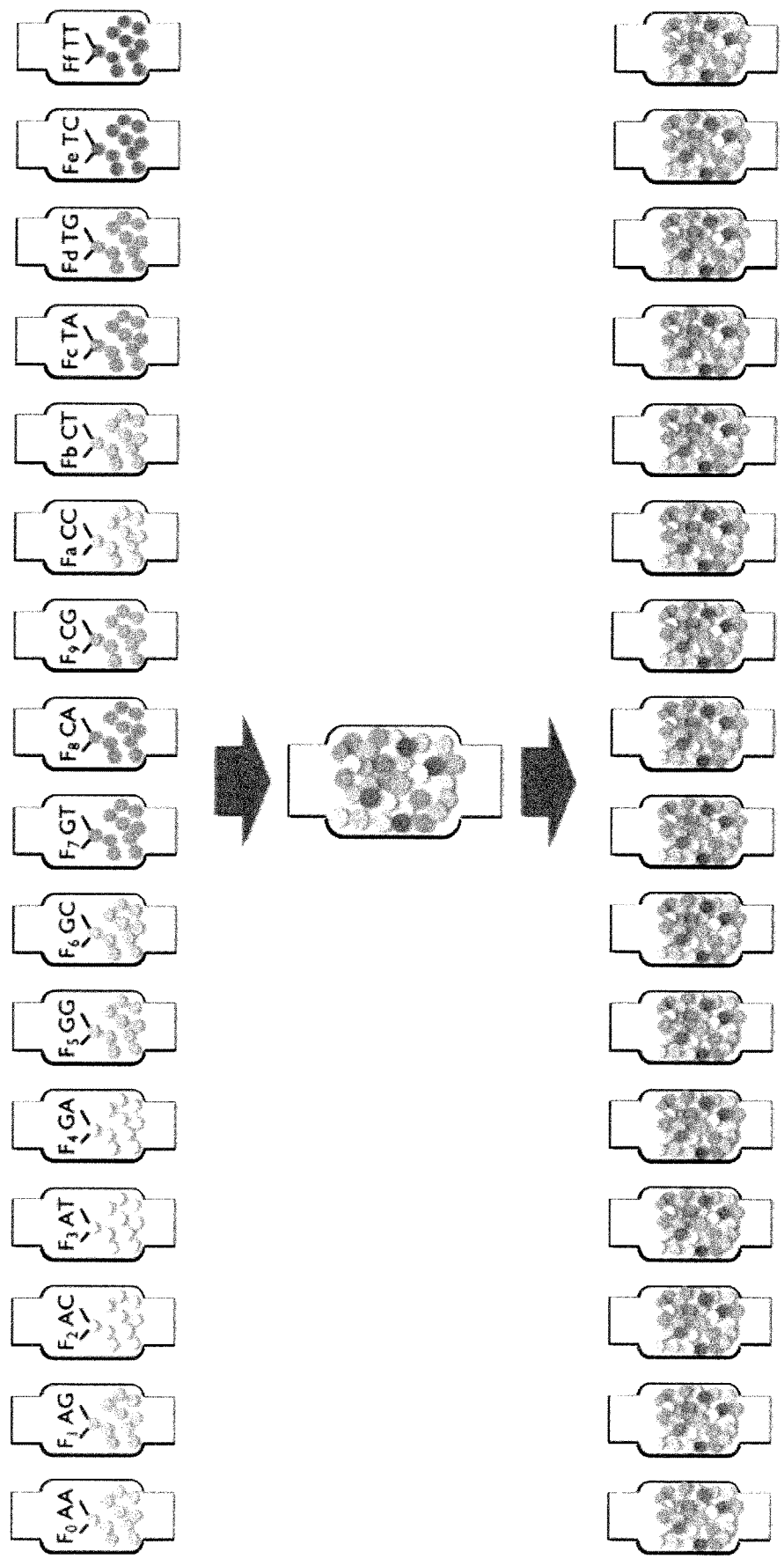

FIGS. 9A and 9B. (A) Illustration of one round of separate extension reactions of a plurality of different oligonucleotide constructs (top row), mixing of constructs (middle row) and splitting of constructs for a further round of extension (bottom row). (B) Coding table for n=2 illustrating the modified nucleotides ($F_x$) that can be added to the functional sequence and corresponding unmodified nucleotide dinucleotide of the coding sequence.

Figure 10A:
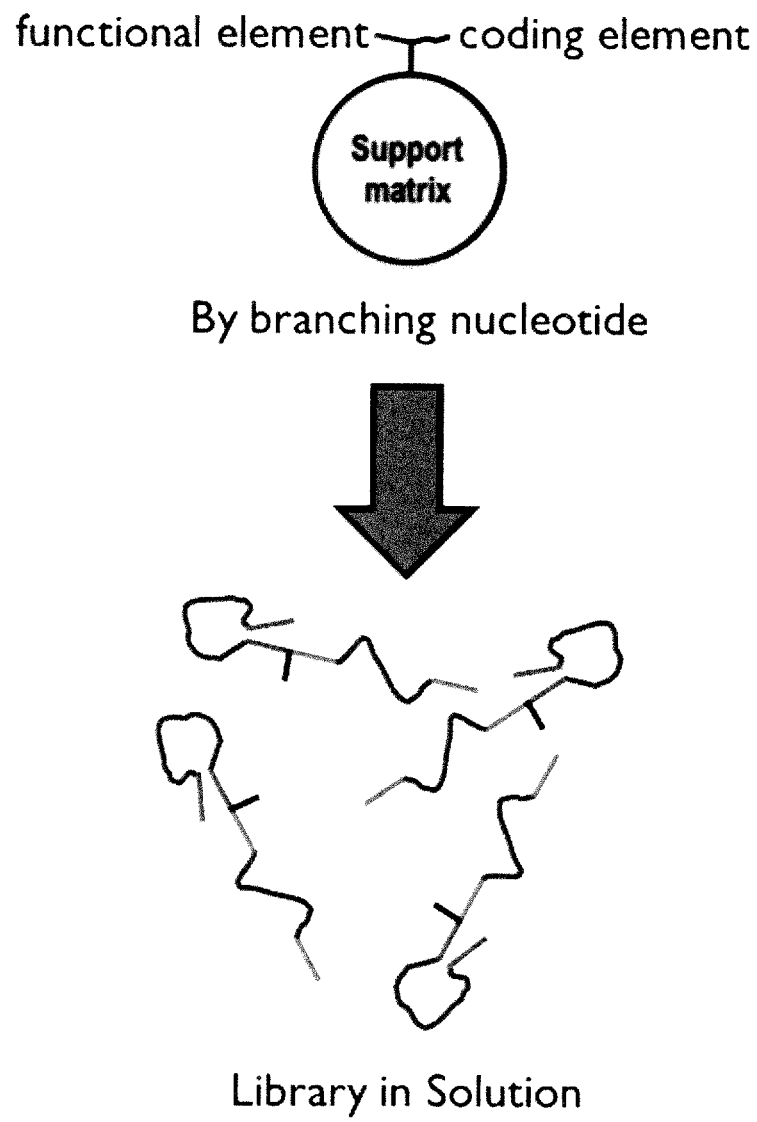
Figure 10B:
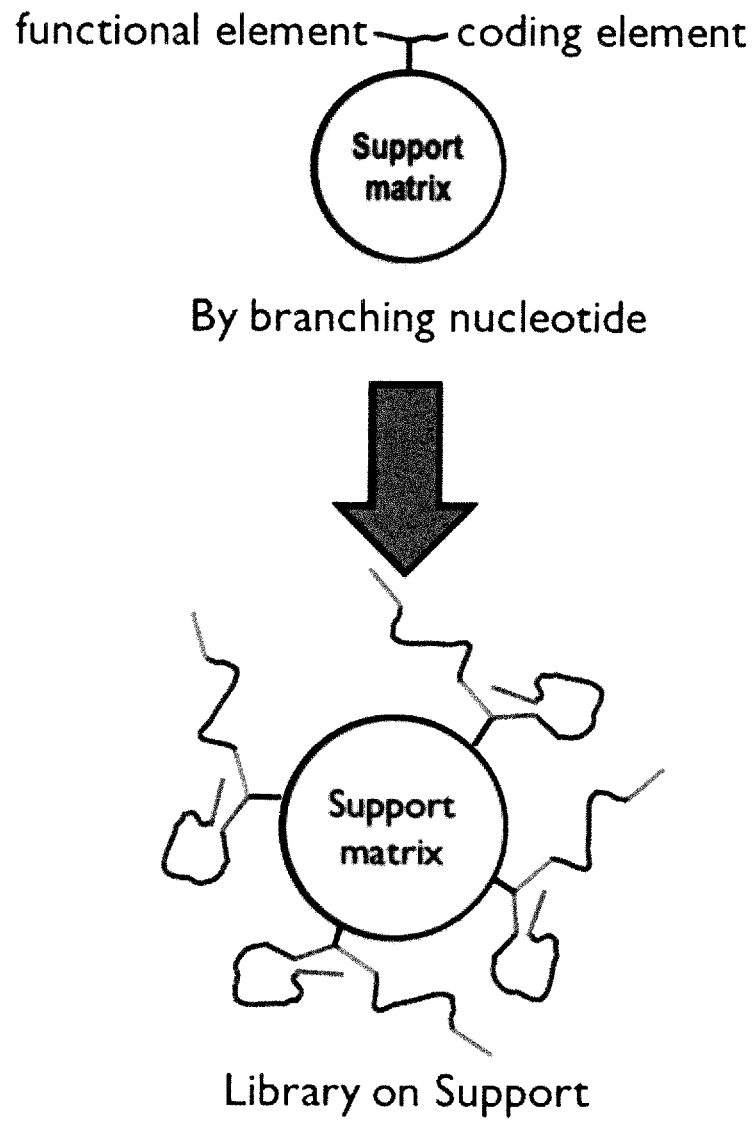
Figure 10C:
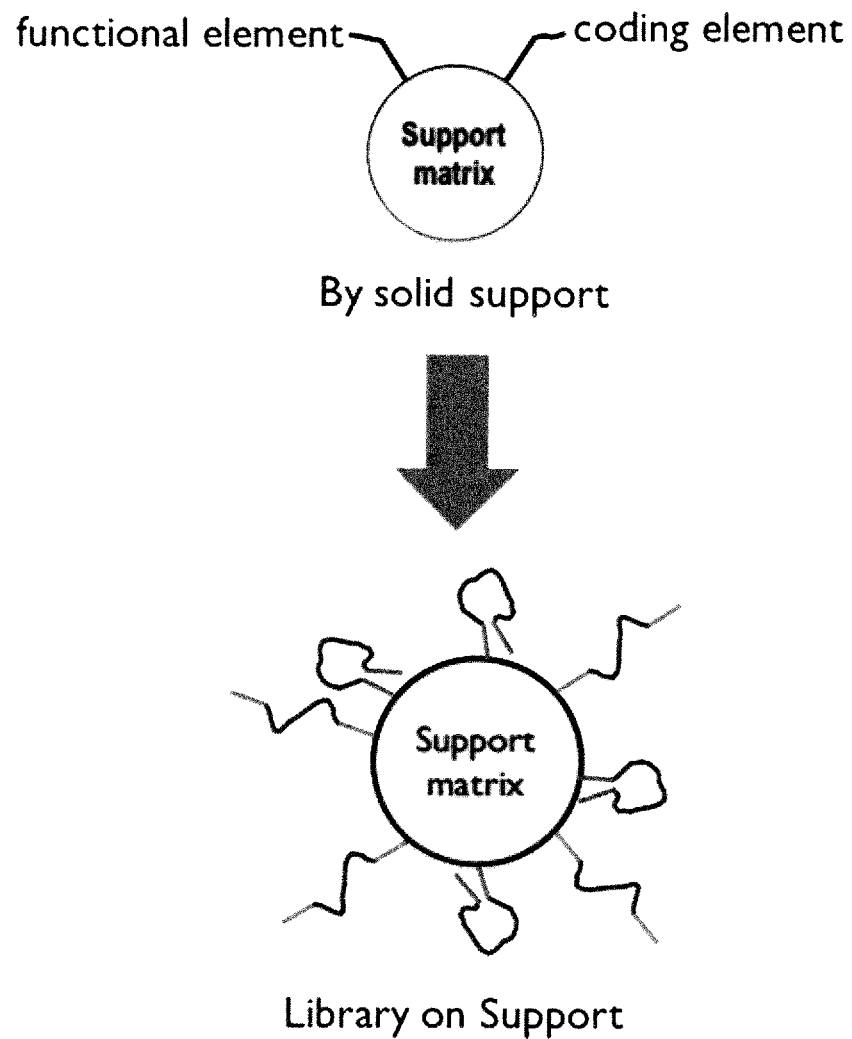

FIGS. 10A, 10B and 10C. (A) Schematic illustration showing synthesis of linear/branched oligonucleotide construct on a support matrix followed by cleavage to generate a library of oligonucleotide constructs in solution. (B) Schematic illustration showing synthesis of linear/branched oligonucleotide construct on a support matrix in which the functional element and coding element are attached to a support matrix via branch moiety and cleavable/non-cleavable linker to generate a library on support matrices each attached to a different oligonucleotide construct. (C) Schematic illustration showing synthesis of oligonucleotide construct in which the functional element and coding element are each attached to a support matrix to generate a library of support matrices each attached to a different oligonucleotide construct.

FIGS. 11A and 11B. Coding tables showing relationship between coding sequence and functional sequence, where n=2. Modified nucleotides are indicated by reference to the base (A, C, G, T) and amino acid substituent by which it is modified (indicated in subscript using the amino acid three letter code). (A) Example of coding table for oligonucleotide constructs according to the present invention, e.g. dinucleotide CA in the coding sequence corresponds to $C_{Phe}$ (Cytosine modified by inclusion of an amino acid residue having the side chain of Phenylalanine) in the functional sequence. (B) Reference example of coding table adapted from U.S. Pat. No. 7,517,646.

Figures 12A, 12B:
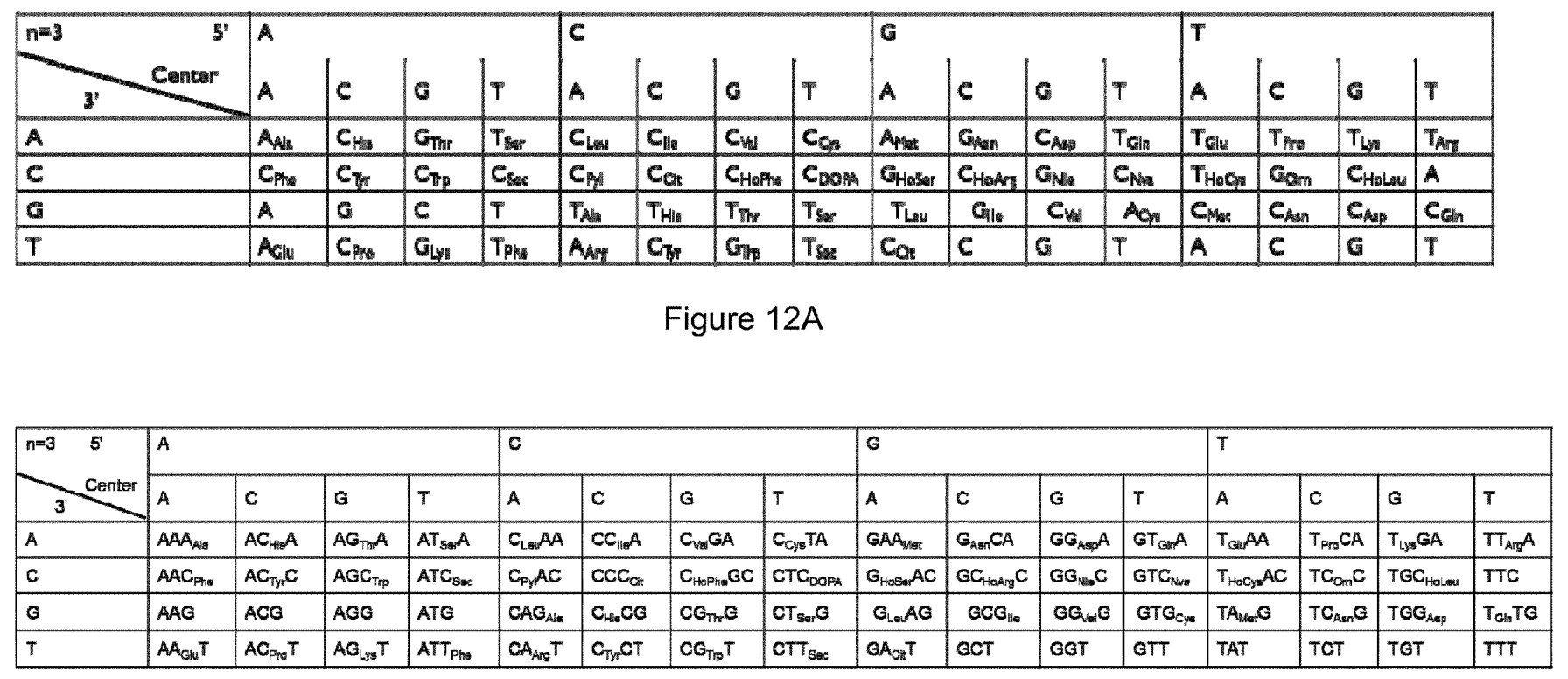

FIGS. 12A and 12B. Coding tables showing relationship between coding sequence and functional sequence, where n=3. Modified nucleotides are indicated by reference to the base (A, C, G, T) and functional substituent by which it is modified (indicated in subscript using abbreviation appeared in this invention). (A) Example of coding table for oligonucleotide constructs according to the present invention, e.g. trinucleotide AAC in the coding sequence corresponds to $C_{Phe}$ (Cytosine modified by inclusion of an amino acid residue having the side chain of Phenylalanine) in the functional sequence. (B) Reference example of coding table adapted from U.S. Pat. No. 7,517,646.

Figure 13:
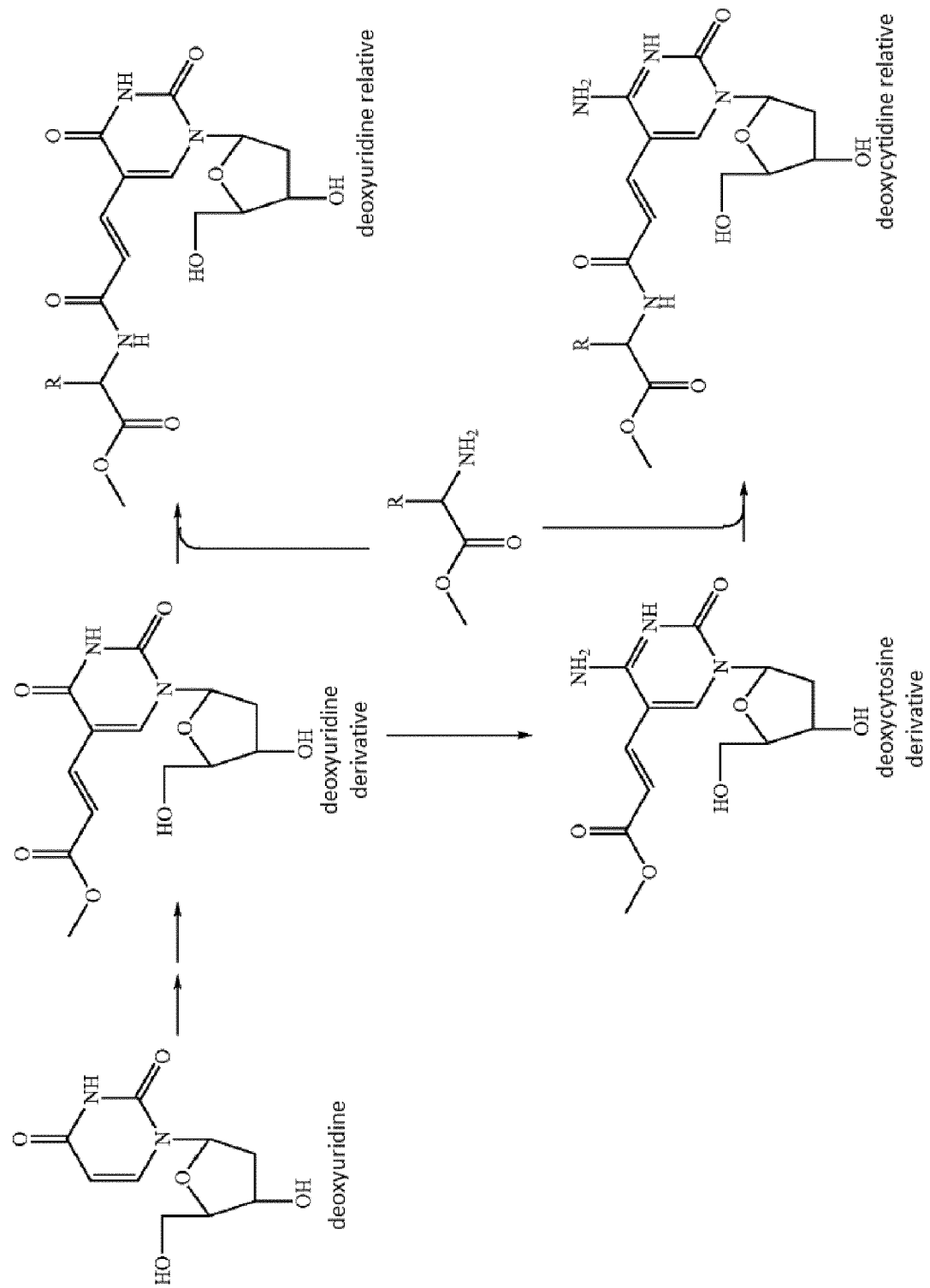

FIG. 13. Synthesis scheme for preparation of deoxyuridine and deoxycytosine modified at the 5-position with an amino acid moiety substituent.

Figures 14, 15:
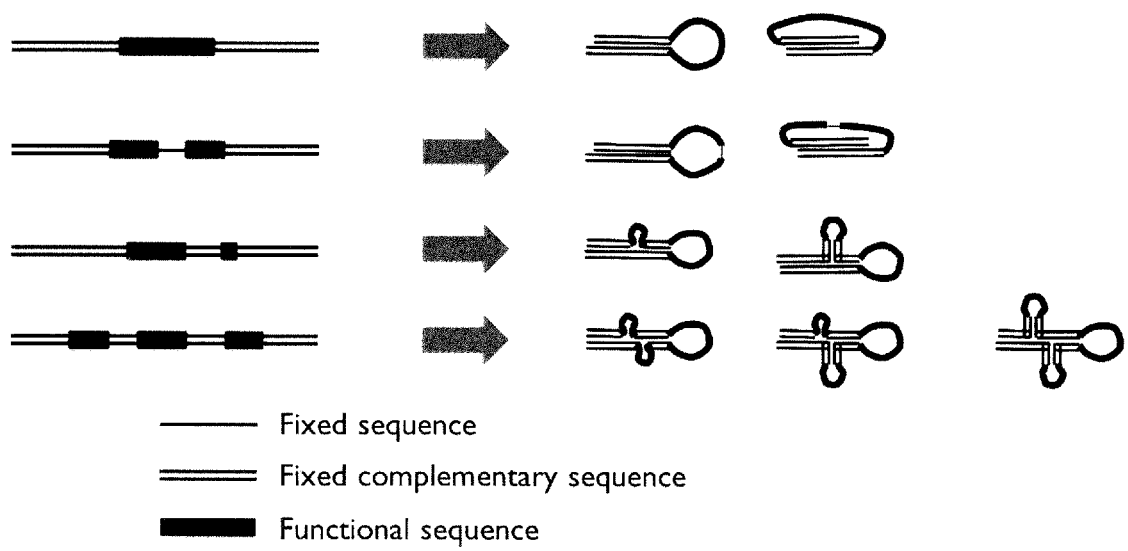

FIG. 14. Coding table of eight 5-position modified deoxyuridines and eight 5-position modified deoxycytosines, where n=2.

FIG. 15. Diagram illustrating alternative configurations of the functional element. A functional sequence flanked by fixed sequences allows formation of a hairpin loop structure. Insertion of additional fixed sequences within the functional sequence permits formation of more complex tertiary structures.

EXAMPLES

Example 1

Eight kinds of deoxycytidine ($C_{1-8}$) and eight kinds of deoxyuridine ($U_{1-8}$) are prepared each having a functional substituent at the 5-position of cytosine or uracil respectively (FIG. 13), in which the functional substituent corresponds to the side chain of an amino acid as follows: 1=Ala, 2=Asp, 3=Glu, 4=Gly, 5=Ile, 6=Lys, 7=Phe, 8=Ser.

Each of the 16 modified nucleosides are one-to-one related to a dinucleotide to form a coding table (FIG. 14).

Example 2—Preparation of Library in Solution

1. A polymer solid support resin having free amino residue on its surface is conjugated with thymidine derivative Formula (B) by dehydration synthesis using HCTU (2-(6-Chloro-1H-benzotriazole-1-yl)-1,1,3,3-tetramethylaminium hexafluorophosphate) as described in Japan patent 5,365,005.

Fomula (B)

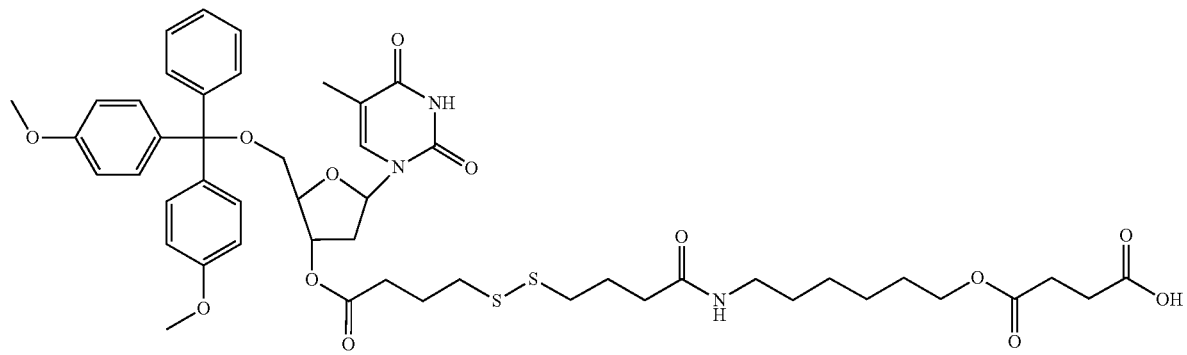

2. The polymer solid support resin is packed in a universal column support.
3. Using a conventional DNA synthesizer and the phosphoramidite procedure, a DMT-thymidine-phosphoramidite is conjugated to the hydroxyl group of the solid support.
4. Glycerol derivative Formula (C) is conjugated with the hydroxyl group of thymidine on the solid support by conventional phosphoramidite method, (1) detritylation, (2) phosphoramidite activation, (3) coupling and capping, and (4) oxidation.

Formula (C)

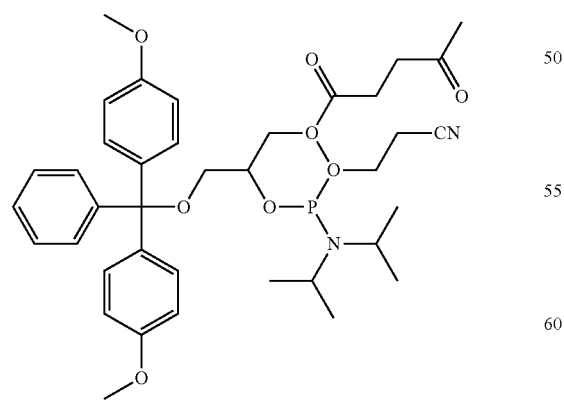

5. DMT-deoxyadenine phosphoramidite, DMT-deoxyguanine phosphoramidite, DMT-deoxycytidine phosphoramidite and DMT-thymine phosphoramidite are used to synthesize a fixed sequence of the functional element from 3' end to 5' direction on DMT-protected hydroxyl group of the glycerol derivative.
6. Lev-deoxyadenine phosphoramidite, Lev-deoxyguanine phosphoramidite, Lev-deoxycytidine phosphoramidite and Lev-thymine phosphoramidite are used to synthesize a fixed sequence of the coding element from 3' to 5' direction on Lev-protected hydroxyl group of the glycerol derivative.
7. The resulting solid supports are removed from the universal support column and packed into 16 new universal support columns.
8. Each of the 16 columns are assigned for addition of 3 nucleotides relating to one cell of the coding table in FIG. 14, e.g. "$\underline{A}$, $\underline{A}$, $U_{Ala}$", "$\underline{C}$, $\underline{A}$, $C_{Ala}$", "$\underline{A}$, $\underline{C}$, $U_{Glu}$", "$\underline{G}$, $\underline{T}$, $U_{Ser}$" etc., (underline=nucleotides added to coding sequence; bold=modified nucleotide added to functional sequence). For example, to add $C_{Ala}$ to the functional sequence and the encoding CA (5' to 3'*) dinucleotide to the coding sequence (according to FIG. 14): $C_{Ala}$ phosphoramidite is added to the functional sequence by deblocking Lev with 0.5M diamine in pyridine/AcOH(1:1); then A is conjugated to the coding sequence by deblocking DMT with 3% TCA in Dichloromethane, and C is then conjugated to the coding sequence by deblocking DMT with 3% TCA in Dichloromethane. [*Note that synthesis by the phosphoramidite method is performed from the 3'-end to the 5'-end.]
9. After treating all 16 columns in the same way using an appropriate combination of nucleotides from each cell of the coding table, the solid supports from the universal support columns, mixed thoroughly, and packed into 16 new universal support columns. In this way, a library of oligonucleotide constructs each having a randomised functional sequence and corresponding coding sequence are prepared in accordance with the coding table.
10. Steps 7 and 8 are repeated as many times as necessary to obtain the desired length of functional sequence.
11. Where fixed sequence(s) are to be incorporated, DMT-deoxyadenine phosphoramidites (e.g. DMT-deoxyguanine phosphoramidite, DMT-deoxycytidine phosphoramidite and DMT-thymine phosphoramidite) are used to synthesise the fixed sequences of the functional element and Lev-phophoramidites are used for synthesis of the fixed sequence of coding element.

12. All protection groups including or excluding DMT and Lev groups are removed using deprotection reagent, such as a hindered base or aqueous ammonia, and cleaved from the solid support using an appropriate cleavage reagent, e.g. TCEP or DTT for a disulfide linker.
13. Purification and desalting are performed according to standard purification methods.

Example 3—Preparation of Library on Support

1. A polymer solid support resin having a free hydroxide residue on its surface is packed in a universal column support.
2. Using a conventional DNA synthesizer and the phosphoramidite procedure, a DMT-thymidine-phosphoramidite is conjugated to a hydroxyl group of the solid support four times so that a thymidine tetranucleotide is tethered on the solid support.
3. After removing DMT by 3% TCA in Dichloromethane, a mixture of DMT-thymine phosphoramidite and Lev-thymine phosphoramidite are conjugated to said thymidine tetraoligonucleotide.
4. By following the steps 4 to 10 of Example 2 ("Library in Solution" preparation), fixed sequences, functional sequences and coding sequence are synthesized.
5. All of the protection groups including DMT and Lev groups are removed using deprotection reagents as indicated in Example 2.
6. The resulting "Library on Support" is recovered from the universal support column.

Example 4—Identification of Oligonucleotide Constructs Binding to a Target Molecule from a Library in Solution Using the Library in Solution ("Library") from Example 2, oligonucleotide constructs that bind with high affinity to a protein target are identified.

A His-tagged PSA (prostate specific antigen) protein (the target molecule) is immobilized on His-Mag Sepharose-Ni bead to immobilize the protein. A suspension of the beads is mixed with the Library solution.

Unbound components in the Library are removed by washing sufficiently with a buffer solution containing high concentration of salt and/or low concentration of mild detergent. After washing, target molecule:oligonucleotide complex is eluted from the His Mag Sepharose-Ni resin by 500 mM imidazole solution.

The recovered target molecule:oligonucleotide complex is subjected to PCR amplification of coding sequence using two primer oligonucleotides complementary to the fixed sequences located at 5' and 3' ends of the coding sequence, respectively. The PCR amplified DNA fraction is subjected to conventional DNA sequencing to obtain sequence information for the coding element, including the coding sequence, and coding table ID sequence.

The coding sequence is translated using the coding table to determine the sequence structure (the base sequence and associated amino acid moiety modifications) of the functional sequence.

Functional sequence oligonucleotide molecules, with or without additional nucleotides providing other functions such as site-specific attachment site, labeling with fluorescent dye and biotinylation, are synthesised by the phosphoramidite method according to the determined sequence structure of the functional sequence. The newly synthesised oligonucleotides are re-assayed for binding to PSA using Surface Plasmon Resonance measurement, sandwich assay and/or affinity column profiling. Varying the conditions for target binding allows selection of functional sequences that exhibit the highest affinity for PSA.

After PCR amplification of target molecule:oligonucleotide complex, the sample is subjected to mild basic conditions to detach the complex, the oligonucleotide fraction is recovered by ethanol precipitation and reapplied for affinity selection described above. This provides a second batch of PCR product for sequencing.

By comparing occurrence of sequences between the first batch, second batch and further re-selection of PCR products, the enrichment process is verified and allows identification of potent candidate sequences.

Example 5—Identification of Oligonucleotide Constructs Binding to a Target Molecule from a Library on Support Using the "Library on Support" ("Library") from Example 3, oligonucleotide constructs that bind with high affinity to a protein target are identified.

PSA (prostate specific antigen) protein (the target molecule) is conjugated with fluorescent dye such as 7-Chloro-4-nitrobenz-2-oxa-1,3-diazole before starting selection process.

Labeled PSA is mixed with suspension of Library overnight. After recovering and washing solid support fraction by filtration, solid support fraction is diluted to optimum concentration for cell sorting equipment (or bead sorting equipment) and each single solid support having stronger fluorescent intensity than threshold is fractionated for recovery.

Each single solid support recovered by sorting equipment is applied for PCR amplification of the coding sequence using two primer oligonucleotides complementary to the fixed sequences located at 5' and 3' ends of the coding sequence, respectively. PCR amplified DNA fraction is subjected to conventional DNA sequencing to obtain sequence information for the coding element, coding sequence, and coding table ID sequence.

The resulting coding sequence is translated using the coding table to determine the sequence structure (the base sequence and associated amino acid moiety modifications) of the functional sequence.

Functional sequence oligonucleotide molecules, with or without additional nucleotides providing other functions such as site-specific attachment site, labeling with fluorescent dye and biotinylation, are synthesised individually by the phosphoramidite method according to the determined sequence structure of the functional sequence. The newly synthesised oligonucleotides are re-assayed for binding to PSA using Surface Plasmon Resonance measurement, sandwich assay and/or affinity column profiling. Varying the conditions for target binding allows selection of functional sequences that exhibit the highest affinity for PSA.

Since one particle of the solid support, e.g. one bead, may have hundreds of thousands of functional elements attached to it, a corresponding number of target molecules may be bound to a single particle. The intensity of fluorescence therefore reflects the statistical value of the result and may be used to characterise the functional element in terms of ability of the functional sequence to contribute to target molecule binding.

The invention claimed is:

1. An oligonucleotide construct comprising a functional element and a coding element, wherein the functional element comprises a functional sequence, the functional sequence comprising a sequence of nucleotides in which one or more, or each, nucleotide is modified and the coding element comprises a coding sequence, the coding sequence comprising a sequence of nucleotides which do not contain the modifications of the functional sequence, wherein the coding sequence encodes the sequence structure of the functional sequence and wherein the coding sequence is an oligonucleotide polymer of n-mers, or a plurality of different n-mers, where n is an integer of 2 or greater and each n-mer corresponds to a single nucleotide in the functional sequence and the coding sequence has n times the number of nucleotides as the functional sequence.

2. The oligonucleotide construct of claim 1, wherein the modified nucleotide(s) of the functional sequence are independently selected to comprise the structure B-L- Func wherein B is independently selected from a pyrimidine or purine base; L is independently selected from a bond or a linker; and Func is a functional substituent.

3. The oligonucleotide construct of claim 1, wherein the functional element and coding element are part of a single linear or branched oligonucleotide.

4. The oligonucleotide construct of claim 1, wherein each of the functional element and coding element are attached to a support matrix.

5. The oligonucleotide construct of claim 1, wherein the functional element comprises the functional sequence flanked by two or more oligonucleotide sequences having partial or complete complementarity to each other.

6. The oligonucleotide construct of claim 1, wherein the coding element comprises the coding sequence flanked by two or more oligonucleotide sequences.

7. The oligonucleotide construct of claim 1, wherein the functional element and coding element are single stranded.

8. A library of oligonucleotide constructs according to claim 1, wherein the library comprises a plurality of oligonucleotide constructs having different sequence structure of the functional sequence.

9. A library of oligonucleotide constructs according to claim 8, wherein the oligonucleotide constructs differ in the base sequence of the functional sequence.

10. A method of preparing an oligonucleotide construct, the oligonucleotide construct comprising a functional element and a coding element, the method comprising:
  (i) extension of a functional element by addition of a single modified nucleotide to form a functional sequence,
  (ii) extension of a coding element by addition of a nucleotide n-mer to form a coding sequence, the n-mer selected to encode the structure of said modified nucleotide of step (i), wherein n is an integer of 2 or greater and the n-mer does not contain the modification of said modified nucleotide of step (i),
  wherein either step (i) or (ii) may be performed first and steps (i) and (ii) are performed sequentially and wherein steps (i) and (ii) are repeated as necessary to produce a coding sequence having a length n times the length of the functional sequence.

11. The method of claim 10, wherein extension of the coding element comprises addition of n nucleotide monomers.

12. The method of claim 10, wherein the oligonucleotide construct is a branched oligonucleotide, wherein the extension in (i) comprises addition of a single modified nucleotide to a branch moiety to form a first branch, and the extension in (ii) comprises addition of a nucleotide n-mer to the branch moiety to form a second branch.

13. The method of claim 10, wherein each oligonucleotide construct is attached to a solid support and preparation of the oligonucleotide constructs is conducted in accordance with a coding table that describes the relationship between each nucleotide added to the functional sequence and the n-mer added to the coding sequence at a corresponding position, wherein each performance of steps (i) and (ii) forms a round of extension, and wherein between rounds of extension the solid supports are mixed and then divided into 2x parts and at least one or each of the 2x parts is subjected to a further round of extension, where x is the number of n-mers in the coding table.

\* \* \* \* \*